(12) United States Patent
Shang et al.

(10) Patent No.: US 8,920,356 B2
(45) Date of Patent: Dec. 30, 2014

(54) CONDUCTIVE POLYMER MATERIALS AND APPLICATIONS THEREOF INCLUDING MONITORING AND PROVIDING EFFECTIVE THERAPY

(75) Inventors: Sherwin Shang, Vernon Hills, IL (US); Ramesh Wariar, Blaine, MN (US); Angel Lasso, Tampa, FL (US); George Lamberson, New Port Richey, FL (US); Dan F. Marcquenski, Jr., Lake Zurich, IL (US); Jan Jensen, Waukegan, IL (US); David Kuhn, Lake Bluff, IL (US); Raf Castellanos, Roselle, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 717 days.

(21) Appl. No.: 13/173,828

(22) Filed: Jun. 30, 2011

(65) Prior Publication Data

US 2011/0264042 A1    Oct. 27, 2011

Related U.S. Application Data

(60) Continuation of application No. 11/626,241, filed on Jan. 23, 2007, now abandoned, which is a division of
(Continued)

(51) Int. Cl.
*A61M 37/00* (2006.01)
*C02F 1/44* (2006.01)
(Continued)

(52) U.S. Cl.
CPC ....... *A61M 1/367* (2013.01); *A61M 2205/6027* (2013.01); *G01N 27/10* (2013.01); *G01N 27/07* (2013.01); *G01N 33/49* (2013.01); *A61M 2205/3317* (2013.01); *A61M 5/16831* (2013.01); *A61M 1/287* (2013.01); *A61M 1/3669* (2013.01); *A61M 1/3656* (2013.01); *A61M 2205/13* (2013.01); *A61M 39/10* (2013.01); *A61M 1/16* (2013.01); *A61M 2205/0233* (2013.01); *A61M 1/3653* (2013.01); *F16L 25/01* (2013.01)
USPC ....... 604/6.08; 604/4.01; 604/6.06; 604/6.16; 604/6.09; 604/6.11; 210/645; 210/739; 210/746

(58) Field of Classification Search
CPC .......... A61M 1/3653; A61M 5/16831; A61M 2205/15
USPC ................ 210/645, 739, 646; 604/5.04, 6.09, 604/6.11, 6.16, 6.06, 6.08
See application file for complete search history.

(56) References Cited

U.S. PATENT DOCUMENTS 3,309,924 A    3/1967  Kolin et al.
3,618,602 A    11/1971 Shaw
(Continued)

FOREIGN PATENT DOCUMENTS

AU    199896231 B2    3/1999
CA    2 175 903       5/1995
(Continued)

OTHER PUBLICATIONS

Mexican Office Action received Oct. 22, 2013 for Application No. MX/a/2011/012455.
(Continued)

*Primary Examiner* — Leslie Deak
(74) *Attorney, Agent, or Firm* — K&L Gates LLP

(57) ABSTRACT

A coupler includes a conductive polymer material that is so constructed and arranged to join tubing, wherein the conductive polymer material includes a conductive polymer component selected from the group consisting of polyaniline, polypyrrole, polythiophenes, polyethylenedioxythiophene, poly (p-phenylene vinylene) and mixtures thereof.

29 Claims, 17 Drawing Sheets

Related U.S. Application Data application No. 10/760,849, filed on Jan. 19, 2004, now abandoned, which is a continuation-in-part of application No. 10/121,006, filed on Apr. 10, 2002, now Pat. No. 7,138,088.

(51) Int. Cl.

| | | |
|---|---|---|
| *G01N 27/10* | (2006.01) | |
| *G01N 27/07* | (2006.01) | |
| *A61M 1/36* | (2006.01) | |
| *A61M 1/16* | (2006.01) | |
| *F16L 25/01* | (2006.01) | |
| *G01N 33/49* | (2006.01) | |
| *A61M 5/168* | (2006.01) | |
| *A61M 1/28* | (2006.01) | |
| *A61M 39/10* | (2006.01) | |

(56) References Cited

U.S. PATENT DOCUMENTS

| | | |
|---|---|---|
| 3,659,591 A | 5/1972 | Doll et al. |
| 3,667,475 A | 6/1972 | Venturelli et al. |
| 3,682,162 A | 8/1972 | Colyer |
| 3,682,172 A | 8/1972 | Freedman et al. |
| 3,699,960 A | 10/1972 | Freedman |
| 3,722,504 A | 3/1973 | Sawyer |
| 3,731,685 A | 5/1973 | Eidus |
| 3,744,636 A | 7/1973 | Commarmot |
| 3,759,247 A | 9/1973 | Doll et al. |
| 3,759,261 A | 9/1973 | Wang |
| 3,778,570 A | 12/1973 | Shuman |
| 3,809,078 A | 5/1974 | Mozes |
| 3,810,140 A | 5/1974 | Finley |
| 3,814,249 A | 6/1974 | Eaton |
| 3,832,067 A | 8/1974 | Kopf et al. |
| 3,832,993 A | 9/1974 | Clipp |
| 3,864,676 A | 2/1975 | Macias et al. |
| 3,867,688 A | 2/1975 | Koski |
| 3,878,095 A | 4/1975 | Frasier et al. |
| 3,882,861 A | 5/1975 | Kettering et al. |
| 3,900,396 A | 8/1975 | Lamadrid |
| 3,946,731 A | 3/1976 | Lichtenstein |
| 3,953,790 A | 4/1976 | Ebling et al. |
| 3,979,665 A | 9/1976 | Ebling et al. |
| 4,010,749 A | 3/1977 | Shaw |
| 4,017,190 A | 4/1977 | Fischel |
| 4,022,211 A | 5/1977 | Timmons et al. |
| 4,026,800 A | 5/1977 | Friedrich et al. |
| 4,055,496 A | 10/1977 | Friedrich et al. |
| 4,060,485 A | 11/1977 | Eaton |
| 4,085,047 A | 4/1978 | Thompson |
| 4,087,185 A | 5/1978 | Lamadrid |
| 4,160,946 A | 7/1979 | Frigato |
| 4,162,490 A | 7/1979 | Fu et al. |
| 4,166,961 A | 9/1979 | Dam et al. |
| 4,167,038 A | 9/1979 | Hennessy |
| 4,181,610 A | 1/1980 | Shintani et al. |
| 4,191,950 A | 3/1980 | Levin et al. |
| 4,192,311 A | 3/1980 | Felfoldi |
| 4,193,068 A | 3/1980 | Ziccardi |
| 4,194,974 A | 3/1980 | Jonsson |
| 4,231,366 A | 11/1980 | Schael |
| 4,231,370 A | 11/1980 | Mroz et al. |
| 4,294,263 A | 10/1981 | Hochman |
| 4,295,475 A | 10/1981 | Torzala |
| 4,303,887 A | 12/1981 | Hill et al. |
| 4,324,687 A | 4/1982 | Louderback et al. |
| 4,327,731 A | 5/1982 | Powell |
| 4,353,368 A | 10/1982 | Slovak et al. |
| 4,354,504 A | 10/1982 | Bro |
| 4,366,051 A | 12/1982 | Fischel |
| 4,399,823 A | 8/1983 | Donnelly |
| 4,399,824 A | 8/1983 | Davidson |
| 4,450,527 A | 5/1984 | Sramek |
| 4,469,593 A | 9/1984 | Ishihara et al. |
| 4,484,135 A | 11/1984 | Ishihara et al. |
| 4,484,573 A | 11/1984 | Yoo |
| 4,501,583 A | 2/1985 | Troutner |
| 4,534,756 A | 8/1985 | Nelson |
| 4,539,559 A | 9/1985 | Kelly et al. |
| 4,559,496 A | 12/1985 | Harnden, Jr. et al. |
| 4,566,990 A | 1/1986 | Liu et al. |
| 4,583,546 A | 4/1986 | Garde |
| 4,648,869 A | 3/1987 | Bobo, Jr. |
| 4,661,093 A | 4/1987 | Beck et al. |
| 4,661,096 A | 4/1987 | Teeple |
| 4,707,906 A | 11/1987 | Posey |
| 4,710,163 A | 12/1987 | Butterfield |
| 4,734,198 A | 3/1988 | Harm et al. |
| 4,739,492 A | 4/1988 | Cochran |
| 4,740,755 A | 4/1988 | Ogawa |
| 4,741,343 A | 5/1988 | Bowman et al. |
| 4,791,932 A | 12/1988 | Margules |
| 4,792,328 A | 12/1988 | Beck et al. |
| 4,796,014 A | 1/1989 | Chia |
| 4,846,792 A | 7/1989 | Bobo, Jr. et al. |
| 4,862,146 A | 8/1989 | McCoy et al. |
| 4,881,413 A | 11/1989 | Georgi et al. |
| 4,898,587 A | 2/1990 | Mera |
| 4,923,613 A | 5/1990 | Chevallet |
| 4,931,051 A | 6/1990 | Castello |
| 4,936,834 A | 6/1990 | Beck et al. |
| 4,938,079 A | 7/1990 | Goldberg |
| 4,959,060 A | 9/1990 | Shimomura et al. |
| 4,965,554 A | 10/1990 | Darling |
| 4,966,729 A | 10/1990 | Carmona et al. |
| 4,976,698 A | 12/1990 | Stokley |
| 4,977,906 A | 12/1990 | Di Scipio |
| 4,979,940 A | 12/1990 | Bobo, Jr. et al. |
| 4,981,467 A | 1/1991 | Bobo, Jr. et al. |
| 5,004,459 A | 4/1991 | Peabody et al. |
| 5,015,958 A | 5/1991 | Masia et al. |
| 5,024,756 A | 6/1991 | Sternby |
| 5,026,348 A | 6/1991 | Venegas |
| 5,030,487 A | 7/1991 | Rosenzweig |
| 5,036,859 A | 8/1991 | Brown |
| 5,039,970 A | 8/1991 | Cox |
| 5,084,026 A | 1/1992 | Shapiro |
| 5,088,990 A | 2/1992 | Hivale et al. |
| 5,100,374 A | 3/1992 | Kageyama |
| 5,121,630 A | 6/1992 | Calvin |
| 5,137,033 A | 8/1992 | Norton |
| 5,139,482 A | 8/1992 | Simeon et al. |
| 5,145,645 A | 9/1992 | Zakin et al. |
| 5,146,414 A | 9/1992 | McKown et al. |
| 5,197,958 A | 3/1993 | Howell |
| 5,200,627 A | 4/1993 | Chevallet |
| 5,202,261 A | 4/1993 | Musho et al. |
| 5,211,201 A | 5/1993 | Kamen et al. |
| 5,225,495 A | 7/1993 | Han et al. |
| 5,247,434 A | 9/1993 | Peterson et al. |
| 5,248,934 A | 9/1993 | Roveti |
| 5,250,439 A | 10/1993 | Musho et al. |
| 5,264,830 A | 11/1993 | Kline et al. |
| 5,266,928 A | 11/1993 | Johnson |
| 5,291,181 A | 3/1994 | DePonte |
| 5,310,507 A | 5/1994 | Zakin et al. |
| 5,314,410 A | 5/1994 | Marks |
| 5,341,127 A | 8/1994 | Smith |
| 5,350,357 A | 9/1994 | Kamen |
| 5,354,289 A | 10/1994 | Mitchell et al. |
| 5,389,093 A | 2/1995 | Howell |
| 5,392,032 A | 2/1995 | Kline et al. |
| 5,395,358 A | 3/1995 | Lu |
| 5,399,295 A | 3/1995 | Gamble et al. |
| 5,416,027 A | 5/1995 | Baudin et al. |
| 5,431,496 A | 7/1995 | Balteau et al. |
| 5,435,010 A | 7/1995 | May |
| 5,439,442 A | 8/1995 | Bellifemine |
| 5,454,374 A | 10/1995 | Omachi |
| 5,468,236 A | 11/1995 | Everhart et al. |
| 5,469,145 A | 11/1995 | Johnson |
| 5,486,286 A | 1/1996 | Peterson et al. |

(56) References Cited

U.S. PATENT DOCUMENTS

| | | | |
|---|---|---|---|
| 5,487,827 A | 1/1996 | Peterson et al. |
| 5,509,822 A | 4/1996 | Negus et al. |
| 5,510,716 A | 4/1996 | Buffaloe, IV et al. |
| 5,510,717 A | 4/1996 | Buffaloe, IV et al. |
| 5,522,809 A | 6/1996 | Larsonneur |
| 5,533,412 A | 7/1996 | Jerman et al. |
| 5,542,932 A | 8/1996 | Daugherty |
| 5,557,263 A | 9/1996 | Fisher et al. |
| 5,567,320 A | 10/1996 | Goux et al. |
| 5,568,128 A | 10/1996 | Nair |
| 5,570,026 A | 10/1996 | Buffaloe, IV et al. |
| 5,570,082 A | 10/1996 | Mahgerefteh et al. |
| 5,571,401 A | 11/1996 | Lewis et al. |
| 5,579,765 A | 12/1996 | Cox et al. |
| 5,602,342 A | 2/1997 | Strandberg |
| 5,603,902 A | 2/1997 | Maltais et al. |
| 5,644,240 A | 7/1997 | Brugger |
| 5,645,734 A | 7/1997 | Kenley et al. |
| 5,649,914 A | 7/1997 | Glaug et al. |
| 5,657,000 A | 8/1997 | Ellingboe |
| 5,670,050 A | 9/1997 | Brose et al. |
| 5,674,390 A | 10/1997 | Matthews et al. |
| 5,674,404 A | 10/1997 | Kenley et al. |
| 5,674,752 A | 10/1997 | Buckley et al. |
| 5,681,298 A | 10/1997 | Brunner et al. |
| 5,685,989 A | 11/1997 | Krivitski et al. |
| 5,690,610 A | 11/1997 | Ito et al. |
| 5,690,624 A | 11/1997 | Sasaki et al. |
| 5,690,821 A | 11/1997 | Kenley et al. |
| 5,698,089 A | 12/1997 | Lewis et al. |
| 5,702,376 A | 12/1997 | Glaug et al. |
| 5,702,377 A | 12/1997 | Collier, IV et al. |
| 5,718,692 A | 2/1998 | Schon et al. |
| 5,726,531 A * | 3/1998 | Hirose et al. ............... 313/509 |
| 5,730,418 A | 3/1998 | Feith et al. |
| 5,744,027 A | 4/1998 | Connell et al. |
| 5,760,694 A | 6/1998 | Nissim et al. |
| 5,760,697 A | 6/1998 | Bruhn et al. |
| 5,762,805 A | 6/1998 | Truitt et al. |
| 5,766,212 A | 6/1998 | Jitoe et al. |
| 5,779,657 A | 7/1998 | Daneshvar |
| 5,788,833 A | 8/1998 | Lewis et al. |
| 5,790,035 A | 8/1998 | Ho |
| 5,790,036 A | 8/1998 | Fisher et al. |
| 5,796,345 A | 8/1998 | Leventis et al. |
| 5,797,892 A | 8/1998 | Glaug et al. |
| 5,800,386 A | 9/1998 | Bellifemine |
| 5,802,814 A | 9/1998 | Sano |
| 5,803,915 A | 9/1998 | Kremenchugsky et al. |
| 5,813,432 A | 9/1998 | Elsdon et al. |
| 5,817,076 A | 10/1998 | Fard |
| 5,838,240 A | 11/1998 | Johnson |
| 5,842,998 A | 12/1998 | Gopakumaran et al. |
| 5,845,644 A | 12/1998 | Hughes et al. |
| 5,847,639 A | 12/1998 | Yaniger |
| 5,862,804 A | 1/1999 | Ketchum |
| 5,863,421 A | 1/1999 | Peter, Jr. et al. |
| 5,868,723 A | 2/1999 | Al-Sabah |
| 5,885,264 A | 3/1999 | Matsushita |
| 5,891,398 A | 4/1999 | Lewis et al. |
| 5,900,726 A | 5/1999 | Brugger et al. |
| 5,900,817 A | 5/1999 | Olmassakian |
| 5,903,222 A | 5/1999 | Kawarizadeh et al. |
| 5,904,671 A | 5/1999 | Navot et al. |
| 5,908,411 A | 6/1999 | Matsunari |
| 5,910,252 A | 6/1999 | Truitt et al. |
| 5,911,706 A | 6/1999 | Estabrook et al. |
| 5,911,872 A | 6/1999 | Lewis et al. |
| 5,931,801 A | 8/1999 | Burbank et al. |
| 5,931,802 A | 8/1999 | Yoshida et al. |
| 5,932,110 A | 8/1999 | Shah et al. |
| 5,938,038 A | 8/1999 | Ziberna |
| 5,938,938 A | 8/1999 | Bosetto et al. |
| 5,941,248 A | 8/1999 | Wheeler |
| 5,947,943 A | 9/1999 | Lee |
| 5,954,691 A | 9/1999 | Prosl |
| 5,954,951 A | 9/1999 | Nuccio |
| 5,959,535 A | 9/1999 | Remsburg |
| 6,009,339 A | 12/1999 | Bentsen et al. |
| 6,015,342 A | 1/2000 | Dennis |
| 6,015,386 A | 1/2000 | Kensey et al. |
| 6,015,387 A | 1/2000 | Schwartz et al. |
| 6,038,914 A | 3/2000 | Carr et al. |
| 6,044,691 A | 4/2000 | Kenley et al. |
| 6,063,042 A | 5/2000 | Navot et al. |
| 6,066,261 A | 5/2000 | Spickermann |
| 6,075,178 A | 6/2000 | La Wilhelm et al. |
| 6,075,367 A | 6/2000 | Brugger |
| 6,077,443 A | 6/2000 | Goldau |
| 6,090,048 A | 7/2000 | Hertz et al. |
| 6,093,869 A | 7/2000 | Roe et al. |
| 6,097,297 A | 8/2000 | Fard |
| 6,113,577 A | 9/2000 | Hakky et al. |
| 6,117,099 A | 9/2000 | Steuer et al. |
| 6,123,847 A | 9/2000 | Bene |
| 6,136,201 A | 10/2000 | Shah et al. |
| 6,139,748 A | 10/2000 | Ericson et al. |
| 6,143,181 A | 11/2000 | Falkvall et al. |
| 6,149,636 A | 11/2000 | Roe et al. |
| 6,153,109 A | 11/2000 | Krivitski |
| 6,160,198 A | 12/2000 | Roe et al. |
| 6,166,639 A | 12/2000 | Pierce et al. |
| 6,167,765 B1 | 1/2001 | Weitzel |
| 6,169,225 B1 | 1/2001 | Otsubo |
| 6,171,289 B1 | 1/2001 | Millot et al. |
| 6,183,437 B1 | 2/2001 | Walker |
| 6,187,199 B1 | 2/2001 | Goldau |
| 6,189,388 B1 | 2/2001 | Cole et al. |
| 6,200,250 B1 | 3/2001 | Janszen |
| 6,206,851 B1 | 3/2001 | Prosl |
| 6,208,880 B1 | 3/2001 | Bentsen et al. |
| 6,210,591 B1 | 4/2001 | Krivitski |
| 6,217,539 B1 | 4/2001 | Goldau |
| 6,221,040 B1 | 4/2001 | Kleinekofort |
| 6,255,396 B1 | 7/2001 | Ding et al. |
| 6,284,131 B1 | 9/2001 | Hogard et al. |
| 6,309,673 B1 | 10/2001 | Duponchelle et al. |
| 6,319,243 B1 | 11/2001 | Becker et al. |
| 6,325,774 B1 | 12/2001 | Bene et al. |
| 6,331,244 B1 | 12/2001 | Lewis et al. |
| 6,372,848 B1 | 4/2002 | Yang et al. |
| 6,386,050 B1 | 5/2002 | Yin et al. |
| 6,387,329 B1 | 5/2002 | Lewis et al. |
| 6,397,661 B1 | 6/2002 | Grimes et al. |
| 6,402,207 B1 | 6/2002 | Segal et al. |
| 6,406,460 B1 | 6/2002 | Hogan |
| 6,445,304 B1 | 9/2002 | Bandeian et al. |
| 6,452,371 B1 | 9/2002 | Brugger |
| 6,461,329 B1 | 10/2002 | Van Antwerp et al. |
| 6,500,154 B1 | 12/2002 | Hakky et al. |
| 6,514,225 B1 | 2/2003 | Utterberg et al. |
| 6,565,525 B1 | 5/2003 | Burbank et al. |
| 6,572,576 B2 | 6/2003 | Brugger et al. |
| 6,575,927 B1 | 6/2003 | Weitzel et al. |
| 6,582,397 B2 | 6/2003 | Alesi et al. |
| 6,585,675 B1 | 7/2003 | O'Mahony et al. |
| 6,595,942 B2 | 7/2003 | Kleinekofort |
| 6,595,943 B1 | 7/2003 | Burbank |
| 6,595,944 B2 | 7/2003 | Balschat et al. |
| 6,607,697 B1 | 8/2003 | Muller |
| 6,610,367 B2 | 8/2003 | Lewis et al. |
| 6,612,624 B1 | 9/2003 | Segal et al. |
| 6,614,212 B2 | 9/2003 | Brugger et al. |
| 6,623,443 B1 | 9/2003 | Polaschegg |
| 6,623,638 B2 | 9/2003 | Watkins et al. |
| 6,663,585 B1 * | 12/2003 | Ender .................. 604/6.08 |
| 6,664,104 B2 | 12/2003 | Pourahmadi et al. |
| 6,683,679 B2 | 1/2004 | Belenkii |
| 6,691,040 B2 | 2/2004 | Bosetto et al. |
| 6,730,233 B2 | 5/2004 | Pedrazzi |
| 6,736,789 B1 | 5/2004 | Spickermann |
| 6,736,811 B2 | 5/2004 | Panescu et al. |
| 6,749,567 B2 | 6/2004 | Davis et al. |
| 6,752,785 B2 | 6/2004 | Van Antwerp et al. |

(56) References Cited

U.S. PATENT DOCUMENTS

| | | |
|---|---|---|
| 6,758,975 B2 | 7/2004 | Peabody et al. |
| 6,759,010 B2 | 7/2004 | Lewis et al. |
| 6,767,333 B1 | 7/2004 | Muller et al. |
| 6,779,396 B2 | 8/2004 | Tsuda et al. |
| 6,794,981 B2 | 9/2004 | Padmanabhan et al. |
| 6,801,041 B2 | 10/2004 | Karinka et al. |
| 6,804,991 B2 | 10/2004 | Balschat et al. |
| 6,806,947 B1 | 10/2004 | Ekdahl et al. |
| 6,827,698 B1 | 12/2004 | Kleinekofort |
| 6,880,404 B2 | 4/2005 | Uberreiter |
| 6,890,315 B1 | 5/2005 | Levin et al. |
| 6,893,879 B2 | 5/2005 | Petersen et al. |
| 6,912,917 B2 | 7/2005 | Brugger et al. |
| 6,924,733 B1 | 8/2005 | McTier et al. |
| 6,932,786 B2 | 8/2005 | Giacomelli et al. |
| 6,979,306 B2 | 12/2005 | Moll |
| 7,011,855 B2 | 3/2006 | Martis et al. |
| 7,022,098 B2 | 4/2006 | Wariar et al. |
| 7,040,142 B2 | 5/2006 | Burbank |
| 7,052,480 B2 | 5/2006 | Han et al. |
| 7,053,059 B2 | 5/2006 | Zieske et al. |
| 7,053,781 B1 | 5/2006 | Haire et al. |
| 7,056,316 B1 | 6/2006 | Burbank et al. |
| 7,060,047 B2 | 6/2006 | Lodi et al. |
| 7,070,591 B2 | 7/2006 | Adams et al. |
| 7,077,819 B1 | 7/2006 | Goldau et al. |
| 7,087,033 B2 | 8/2006 | Brugger et al. |
| 7,115,107 B2 | 10/2006 | Delnevo et al. |
| 7,138,088 B2 | 11/2006 | Wariar et al. |
| 7,147,615 B2 | 12/2006 | Wariar et al. |
| 7,172,569 B2 | 2/2007 | Kleinekofort |
| 7,172,570 B2 | 2/2007 | Cavalcanti et al. |
| 7,176,344 B2 | 2/2007 | Gustafson et al. |
| 7,217,251 B2 | 5/2007 | Olsen et al. |
| 7,230,687 B2 | 6/2007 | O'Mahony et al. |
| 7,276,041 B2 | 10/2007 | Moll |
| 7,278,991 B2 | 10/2007 | Morris et al. |
| 7,291,123 B2 | 11/2007 | Baraldi et al. |
| 2001/0004523 A1 | 6/2001 | Bosetto et al. |
| 2002/0036375 A1 | 3/2002 | Matsuda |
| 2002/0042125 A1 | 4/2002 | Petersen et al. |
| 2002/0055167 A1 | 5/2002 | Pourahmadi et al. |
| 2002/0088752 A1 | 7/2002 | Balschat et al. |
| 2002/0120260 A1 | 8/2002 | Morris et al. |
| 2002/0120261 A1 | 8/2002 | Morris et al. |
| 2002/0121471 A1 | 9/2002 | Pedrazzi |
| 2002/0141901 A1 | 10/2002 | Lewis et al. |
| 2002/0162778 A1 | 11/2002 | Peabody et al. |
| 2002/0173731 A1 | 11/2002 | Martin et al. |
| 2002/0188206 A1 | 12/2002 | Davis et al. |
| 2002/0190839 A1 | 12/2002 | Padmanabhan et al. |
| 2002/0197390 A1 | 12/2002 | Lewis et al. |
| 2002/0198483 A1 | 12/2002 | Wariar et al. |
| 2003/0009123 A1 | 1/2003 | Brugger et al. |
| 2003/0016002 A1 | 1/2003 | Brugger et al. |
| 2003/0036719 A1 | 2/2003 | Giacomelli et al. |
| 2003/0075498 A1 | 4/2003 | Watkins et al. |
| 2003/0083901 A1 | 5/2003 | Bosch et al. |
| 2003/0093069 A1 | 5/2003 | Panescu et al. |
| 2003/0094369 A1 | 5/2003 | Tolley et al. |
| 2003/0126910 A1 | 7/2003 | Burbank |
| 2003/0128125 A1 | 7/2003 | Burbank et al. |
| 2003/0128126 A1 | 7/2003 | Burbank et al. |
| 2003/0138501 A1 | 7/2003 | Elisabettini et al. |
| 2003/0152482 A1 | 8/2003 | O'Mahony et al. |
| 2003/0176829 A1 | 9/2003 | Lodi et al. |
| 2003/0194894 A1 | 10/2003 | Wariar et al. |
| 2003/0195453 A1 | 10/2003 | Han et al. |
| 2003/0195454 A1 | 10/2003 | Wariar et al. |
| 2004/0054352 A1 | 3/2004 | Adams et al. |
| 2004/0113801 A1 | 6/2004 | Gustafson et al. |
| 2004/0171977 A1 | 9/2004 | Paolini et al. |
| 2004/0185709 A1 | 9/2004 | Williams, Jr. et al. |
| 2004/0186409 A1 | 9/2004 | Cavalcanti et al. |
| 2004/0186415 A1 | 9/2004 | Burbank et al. |
| 2004/0201216 A1 | 10/2004 | Segal et al. |
| 2004/0243046 A1 | 12/2004 | Brugger et al. |
| 2004/0254513 A1 | 12/2004 | Shang et al. |
| 2005/0010118 A1 | 1/2005 | Toyoda et al. |
| 2005/0010157 A1* | 1/2005 | Baraldi et al. ............... 604/4.01 |
| 2005/0038325 A1 | 2/2005 | Moll |
| 2005/0096578 A1 | 5/2005 | Kleinekofort |
| 2005/0131332 A1 | 6/2005 | Kelly et al. |
| 2005/0230313 A1 | 10/2005 | O'Mahony et al. |
| 2005/0241387 A1 | 11/2005 | Miesel et al. |
| 2005/0242034 A1 | 11/2005 | Connell et al. |
| 2005/0245858 A1 | 11/2005 | Miesel et al. |
| 2005/0245887 A1 | 11/2005 | Olsen et al. |
| 2005/0256451 A1 | 11/2005 | Adams et al. |
| 2005/0256455 A1 | 11/2005 | Adams et al. |
| 2006/0012774 A1 | 1/2006 | O'Mahony et al. |
| 2006/0064159 A1 | 3/2006 | Porter et al. |
| 2006/0069339 A1 | 3/2006 | Moll |
| 2006/0081517 A1 | 4/2006 | Toyoda et al. |
| 2006/0087120 A1 | 4/2006 | Segal et al. |
| 2006/0116623 A1 | 6/2006 | Han et al. |
| 2006/0130591 A1 | 6/2006 | Perkins |
| 2006/0166548 A1 | 7/2006 | Williams, Jr. et al. |
| 2006/0184087 A1 | 8/2006 | Wariar et al. |
| 2007/0004996 A1 | 1/2007 | Lovejoy et al. |
| 2007/0010779 A1 | 1/2007 | Utterberg et al. |
| 2007/0066928 A1 | 3/2007 | Lannoy |
| 2008/0065006 A1 | 3/2008 | Roger |
| 2008/0195021 A1 | 8/2008 | Roger |
| 2008/0195060 A1 | 8/2008 | Roger |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0088612 A1 | 4/2009 | Bouton |
| 2009/0088613 A1 | 4/2009 | Marttila |
| 2009/0088683 A1 | 4/2009 | Roger |
| 2009/0105627 A1 | 4/2009 | Rohde |
| 2010/0022934 A1 | 1/2010 | Hogard |
| 2010/0022935 A1 | 1/2010 | Muller |

FOREIGN PATENT DOCUMENTS

| | | |
|---|---|---|
| CA | 2519423 | 9/2004 |
| CA | 2535502 | 3/2005 |
| CA | 2 282 628 | 11/2006 |
| DE | 28 38 414 | 3/1980 |
| DE | 29 48 768 A1 | 6/1981 |
| DE | 30 45 514 A1 | 7/1982 |
| DE | 32 23 086 A1 | 7/1983 |
| DE | 34 40 584 A1 | 5/1986 |
| DE | 3 639 797 C1 | 2/1988 |
| DE | 38 23 859 A1 | 1/1990 |
| DE | 38 36 712 A1 | 5/1990 |
| DE | 39 09 548 | 9/1990 |
| DE | 40 00 961 A1 | 7/1991 |
| DE | 40 14 572 A1 | 11/1991 |
| DE | 40 18 953 A1 | 1/1992 |
| DE | 40 23 336 A1 | 2/1992 |
| DE | 42 39 937 C2 | 6/1994 |
| DE | 4239937 | 8/1995 |
| DE | 19746367 | 6/1998 |
| DE | 197 28 031 A1 | 1/1999 |
| DE | 197 39 099 | 1/1999 |
| DE | 19 82 3836 | 12/1999 |
| DE | 199 01 078 C1 | 2/2000 |
| DE | 10100146 | 7/2001 |
| DE | 10100146 | 7/2002 |
| EP | 0032906 | 8/1981 |
| EP | 0089875 | 9/1983 |
| EP | 0 270 048 B1 | 6/1988 |
| EP | 0 272 414 | 6/1988 |
| EP | 0 287 485 A1 | 10/1988 |
| EP | 0 328 162 B1 | 8/1989 |
| EP | 0 328 163 B1 | 8/1989 |
| EP | 0 332 330 B1 | 9/1989 |

(56) References Cited

FOREIGN PATENT DOCUMENTS

| | | |
|---|---|---|
| EP | 0259 551 | 9/1990 |
| EP | 332330 | 2/1993 |
| EP | 0 542 140 A2 | 5/1993 |
| EP | 0 551 043 | 7/1993 |
| EP | 0 472 798 | 3/1994 |
| EP | 0 584 557 A1 | 3/1994 |
| EP | 0 590 810 | 4/1994 |
| EP | 0 611 228 | 8/1994 |
| EP | 688 531 | 12/1995 |
| EP | 0705611 | 4/1996 |
| EP | 0 551 043 B1 | 7/1996 |
| EP | 0 745 400 | 12/1996 |
| EP | 0 820 776 A2 | 1/1998 |
| EP | 0 835 669 A2 | 4/1998 |
| EP | 0 845 273 A1 | 6/1998 |
| EP | 0 846 470 A1 | 6/1998 |
| EP | 0 590 810 B1 | 7/1998 |
| EP | 0 895 787 A1 | 2/1999 |
| EP | 0 898 975 A1 | 3/1999 |
| EP | 0 898 976 A1 | 3/1999 |
| EP | 0 611 228 B1 | 4/1999 |
| EP | 0 911 044 A1 | 4/1999 |
| EP | 0930080 | 7/1999 |
| EP | 0943369 | 9/1999 |
| EP | 0 745 400 B1 | 12/1999 |
| EP | 0980513 | 2/2000 |
| EP | 1019118 | 7/2000 |
| EP | 1156841 | 11/2001 |
| EP | 1395314 | 3/2004 |
| EP | 1 401 518 | 3/2006 |
| EP | 1706731 | 10/2006 |
| EP | 10075427 | 12/2010 |
| FR | 2 680 678 A1 | 3/1993 |
| FR | 2 737 124 | 1/1997 |
| GB | 2 069 702 A | 8/1981 |
| GB | 2 145 859 A | 4/1985 |
| GB | 2 177 247 A | 1/1987 |
| GB | 2 250 121 A | 5/1992 |
| JP | 55031407 | 3/1980 |
| JP | 56080257 | 7/1981 |
| JP | 57-044845 | 3/1982 |
| JP | 62042047 A | 2/1987 |
| JP | 62-54157 | 3/1987 |
| JP | 64-052473 | 2/1989 |
| JP | 01250733 | 10/1989 |
| JP | 4008361 | 1/1992 |
| JP | 5237184 | 9/1993 |
| JP | 6178789 | 6/1994 |
| JP | 8-98881 | 4/1996 |
| JP | 0-28791 | 2/1997 |
| JP | 10-201842 | 4/1998 |
| JP | 10211278 A | 8/1998 |
| JP | 11104233 A | 4/1999 |
| JP | 11-267197 | 10/1999 |
| JP | 11290452 | 10/1999 |
| JP | 11299889 A | 11/1999 |
| JP | 2000-131286 | 5/2000 |
| JP | 2000-140092 | 5/2000 |
| JP | 2001-208710 | 8/2001 |
| JP | 2001-515766 | 9/2001 |
| JP | 2003-518413 | 6/2003 |
| JP | 2004-521707 | 7/2004 |
| JP | 2004-521708 | 7/2004 |
| JP | 2006 055588 | 3/2006 |
| JP | 2006-507024 | 3/2006 |
| JP | 2006 110118 | 4/2006 |
| JP | 2006-110120 | 4/2006 |
| JP | 2006-511244 | 4/2006 |
| JP | 2006-512101 | 4/2006 |
| JP | 2007-000621 | 1/2007 |
| JP | 2007-020801 | 2/2007 |
| NZ | 337335 | 5/2001 |
| TW | 249204 | 6/1995 |
| WO | WO 81/00295 | 2/1981 |
| WO | WO 86/04710 | 8/1986 |
| WO | WO 89/12228 | 12/1989 |
| WO | WO 94/02918 | 2/1994 |
| WO | WO 94/07224 | 3/1994 |
| WO | WO 95/12545 | 5/1995 |
| WO | WO 96/25904 | 8/1996 |
| WO | WO 97/02057 | 1/1997 |
| WO | WO 97/03712 | 2/1997 |
| WO | WO 97/10013 | 3/1997 |
| WO | WO 98/32476 | 7/1998 |
| WO | WO 98/38485 | 9/1998 |
| WO | WO 99/12588 | 3/1999 |
| WO | WO 99/24145 | 5/1999 |
| WO | WO 99/26686 | 6/1999 |
| WO | WO 99/29356 | 6/1999 |
| WO | WO 99/42151 | 8/1999 |
| WO | WO 00/38761 | 7/2000 |
| WO | WO 01/06975 A1 | 2/2001 |
| WO | WO 01/24854 A1 | 4/2001 |
| WO | 01/47581 | 7/2001 |
| WO | WO 01/47581 A1 | 7/2001 |
| WO | WO 02/098543 A1 | 12/2002 |
| WO | WO 03/000315 | 1/2003 |
| WO | WO 03/002174 | 1/2003 |
| WO | WO 03/006944 | 1/2003 |
| WO | WO 03/086504 | 10/2003 |
| WO | WO 03/086505 | 10/2003 |
| WO | WO 03/086506 A1 | 10/2003 |
| WO | WO 2004/082740 | 9/2004 |
| WO | WO 2004/084972 | 10/2004 |
| WO | WO 2004/108192 | 12/2004 |
| WO | WO 2004/108206 A1 | 12/2004 |
| WO | WO 2005/019416 | 3/2005 |
| WO | WO 2005/046439 | 5/2005 |
| WO | WO 2005/105199 | 11/2005 |
| WO | WO 2005/105200 | 11/2005 |
| WO | WO 2006/001759 | 1/2006 |
| WO | WO 2006/044677 | 4/2006 |
| WO | 2006/138359 | 12/2006 |
| WO | WO 2008/100675 | 8/2008 |

OTHER PUBLICATIONS

European Office Action dated Dec. 20, 2013 for Application No. 03 723 889.6-1662.
International Search Report ("ISR") issued by the European Patent Office as the International Searching Authority and pertaining to International Application PCT/US03/10190 having an International filing date of Apr. 2, 2003, and naming Baxter International Inc. and Baxter Healthcare S.A. as the Applicants.
Notification Concerning Transmittal of International Preliminary Report on Patentability for International Application No. PCT/US2008/051289 mailed on Aug. 27, 2009.
International Search Report for International Application No. PCT/US2008/051289 dated Jun. 9, 2008.
Machine Translation of EP 0542 140 (1993).
Translation of JP 87-42047, Feb. 24, 1987.
Translation of EPO 0542140, Jun. 11, 1992.
Definition of Disperse http://dictionary.reference.com/browse/disperse 2009.
http://dictionary.reference.com/browse/pivot 2011.
European Office Action for Application No. 10 075 427.4-2320 dated Jan. 25, 2013.
Japanese Office Action dated Nov. 21, 2013 for Application No. 2012-272276.
Japanese Office Action dated Dec. 2, 2013 for Application No. 2013-007007.
European Office Action for App. No. 10 075 482.9-1662 dated Feb. 27, 2013.
Office Action for Mexican Patent Application PA/a/2009/008502 mailed Jun. 6, 2012.
Office Action for Mexican Patent Application PA/a/2006/008140 mailed May 21, 2012.
Office Action for Japanese Patent Application No. 2010-055110 mailed May 30, 2012.
Office Action for European Patent Application No. 03723889.6 dated May 23, 2012.

(56) References Cited

OTHER PUBLICATIONS

Office Action for European Divisional Patent Application No. 10075427.4 dated May 30, 2012.
Search Report for Divisional European Application No. 10075380.5 dated Jul. 16, 2012.
Office Action for European Patent Application No. 10075482.9 dated Jul. 27, 2012.
Office Action for European Patent Application No. 08727811.5 dated Jul. 18 2012.
Office Action for Japanese Application No. 2009-206484 sent Aug. 22, 2012.
European Office Action dated Jun. 18, 2013 for Application No. 03 723 889.6-1662.
Office Action for Japanese Application No. 2009-549652 received Sep. 14, 2012.
Office Action for Japanese Application No. 2010-055110 dated Oct. 25, 2012.
European Search Report for Application No. 12170615.4-2320 dated Oct. 30, 2012.
Extended European Search Report for European Application No. 10075482.9 mailed on Feb. 2, 2011.
Japanese Office Action for Application No. 2009-206484 mailed Mar. 1, 2012.
Notification Concerning Transmittal of International Preliminary Report on Patentability for International Application No. PCT/US2008/051289 dated Aug. 19, 2009.
Office Action for Japanese Application No. 2010-55110 mailed Apr. 26, 2013.
Canadian Office Action dated Mar. 4, 2014 for Application No. 2,673,877.
Japanese Office Action dated Mar. 10, 2014 for Application No. 2013-007077.
European Office Action dated Mar. 21, 2014 for Application No. 10 075 380.5-1662.
Publication for Opposition No. 4-22586 (Partially corresponding to US4469593) dated Apr. 17, 1992.
Utility Model Publication for Opposition No. 63-9287 dated Mar. 18, 1988.
Japanese Office Action dated Sep. 11, 2014 for Application No. 2013-034343.

\* cited by examiner

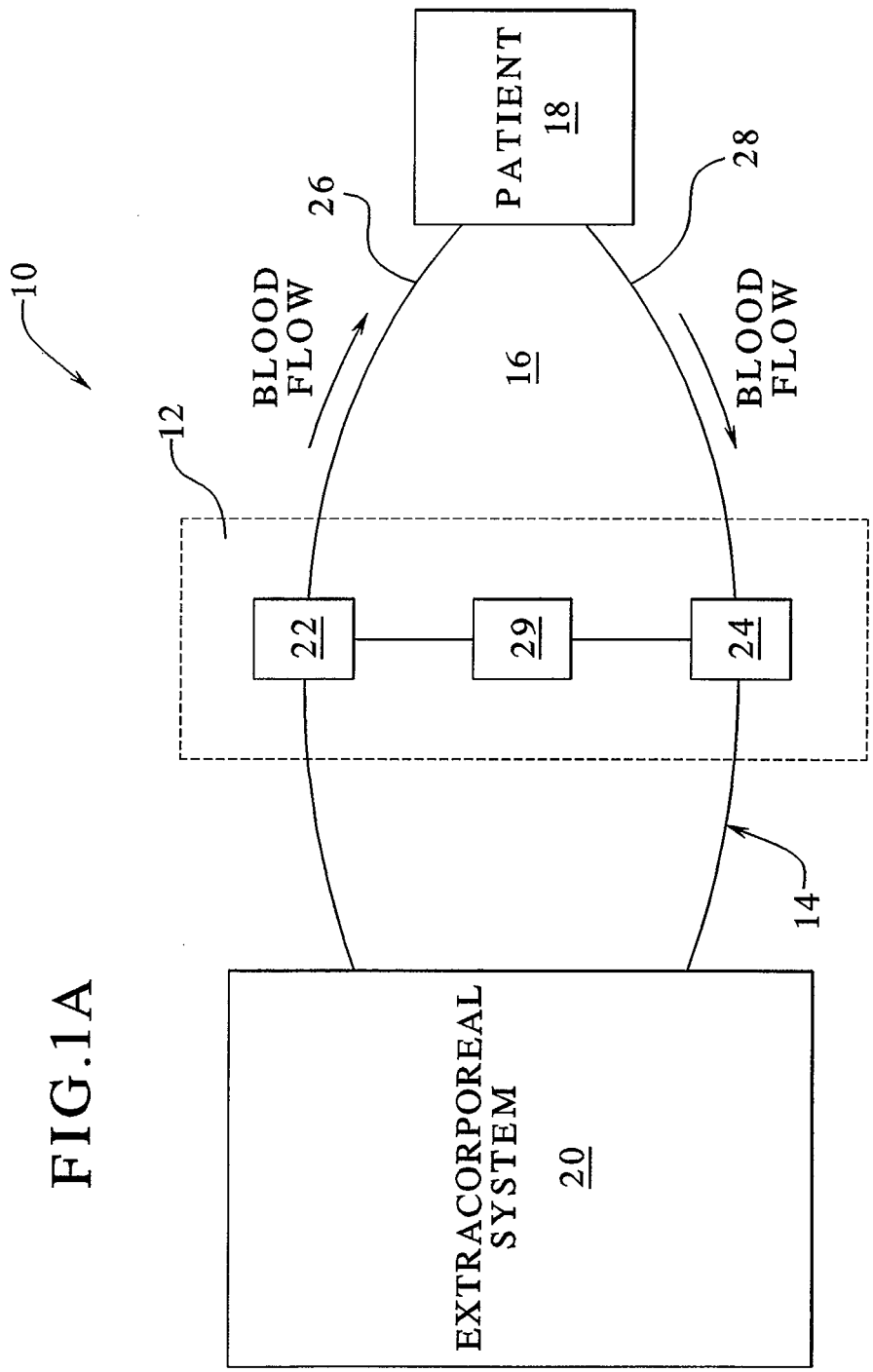

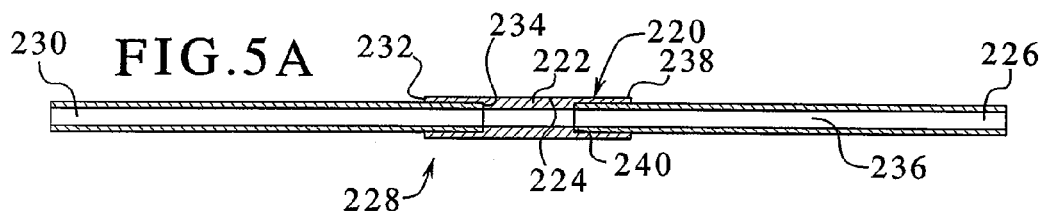
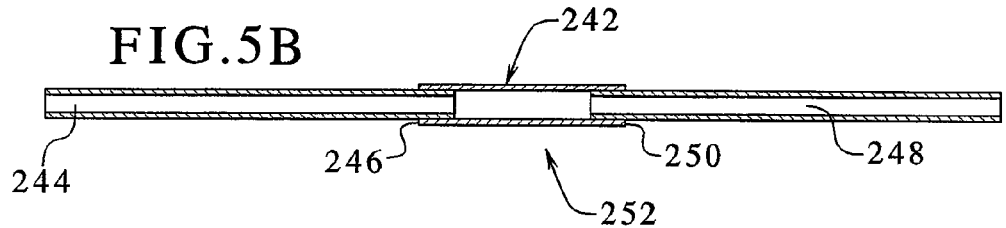
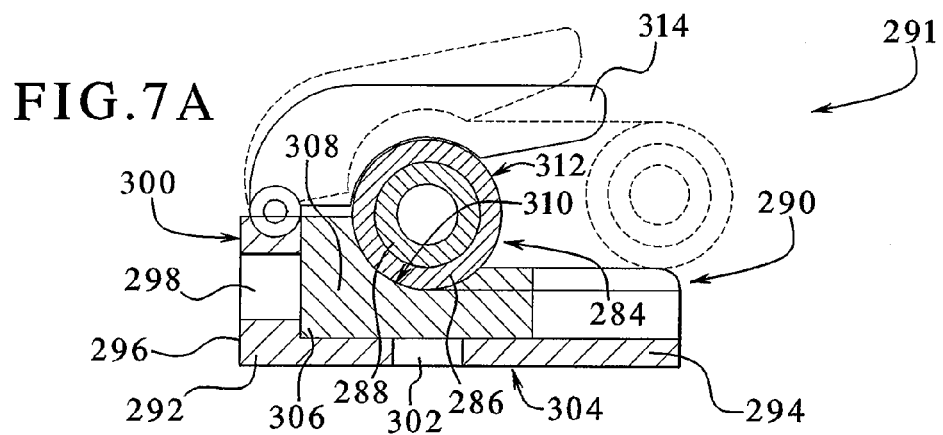
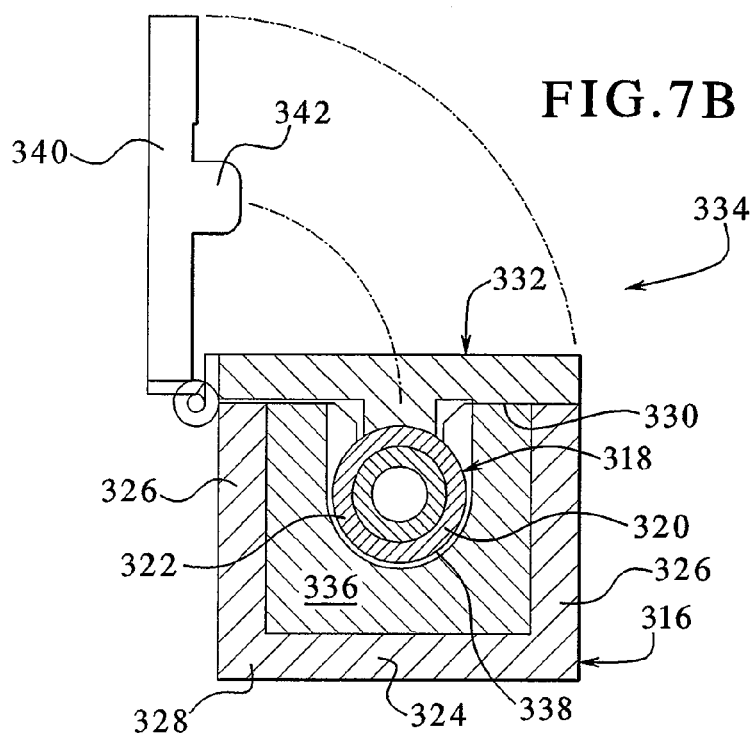

CONDUCTIVE POLYMER MATERIALS AND APPLICATIONS THEREOF INCLUDING MONITORING AND PROVIDING EFFECTIVE THERAPY

CROSS REFERENCE TO RELATED APPLICATIONS

This application is a continuation of patent application Ser. No. 11/626,241, filed on Jan. 23, 2007, now abandoned, which is a divisional of patent application Ser. No. 10/760,849, filed Jan. 19, 2004, now abandoned, which is a continuation-in-part of U.S. patent application Ser. No. 10/121,006 filed on Apr. 10, 2002, now U.S. Pat. No. 7,138,088, issued Nov. 21, 2006, the entire disclosures of which are incorporated by reference.

BACKGROUND OF THE INVENTION

The present invention relates generally to conductive polymer materials and methods of preparing and employing same. More specifically, the present invention relates to conductive polymer materials and applications thereof including monitoring patient access disconnection, monitoring solution mixing and compounding and the like during medical therapy, such as dialysis therapy.

A variety of different medical treatments relate to the delivery of fluid to and/or from a patient, such as the delivery of blood between a patient and an extracorporeal system connected to the patient via a needle or needles or any suitable access device inserted within the patient. For example, hemodialysis, hemofiltration and hemodiafiltration are all treatments that remove waste, toxins and excess water directly from the patient's blood. During these treatments, the patient is connected to an extracoporeal machine, and the patient's blood is pumped through the machine. Waste, toxins and excess water are removed from the patient's blood, and the blood is infused back into the patient. Needles or other suitable access devices are inserted into the patient's vascular access in order to transfer the patient's blood to and from the extracorporeal machine. Traditional hemodialysis, hemofiltration and hemodiafiltration treatments can last several hours and are generally performed in a treatment center about three to four times per week.

During any of these hemo treatments, dislodgment of the access device can occur, such as dislodgment of a needle inserted into the patient's vascular access including an arterio-venous graft or fistula. If not detected immediately, this can produce a significant amount of blood loss to the patient. The risks associated with a needle dislodgment are considerable. In this regard, important criteria for monitoring blood loss include, for example, the sensitivity, specificity and response time with respect to the detection of needle dislodgment. With increased levels of sensitivity, specificity, and response time, the detection of needle dislodgment can be enhanced, and blood loss due to dislodgment can be minimized.

Typically, patients undergoing medical treatment, such as hemodialysis, hemofiltration or hemodiafiltration, are visually monitored in order to detect needle dislodgment. However, the needle may not be in plain view of the patient or medical staff (i.e., it may be covered by a blanket) such that it could delay detection and, thus, responsive actions to be taken in view of dislodgment, such as stopping the blood pump of the extracorporeal machine to minimize blood loss to the patient.

Moreover, in view of the increased quality of life, observed reductions in both morbidity and mortality and lower costs than in-center treatments, a renewed interest has arisen for self care and home hemo therapies. Such home hemo therapies (whether hemodialysis, hemofiltration or hemodiafiltration) allow for both nocturnal as well as daily treatments. During these self care and home hemo sessions, especially during a nocturnal home hemo session, when the patient is asleep, dislodgment risks are more significant because nurses or other attendants are not present to detect the dislodgment.

Although devices that employ a variety of different sensors are available and known for detecting and/or monitoring a variety of different bodily fluids, these devices may not be suitably adapted to detect needle dislodgment. For example, known devices that employ sensors including pH, temperature and conductivity have been utilized to detect bedwetting and diaper wetness. Further, devices that employ pressure sensors and/or flow sensing devices are known and used during medical treatment, such as dialysis therapy, to monitor fluid flow including blood flow to and/or from the patient. However, these types of detection devices may not provide an adequate level of sensitivity and responsiveness if applied to detecting blood loss from the patient due to needle dislodgment. Although venous pressure is known to be used to monitor needle dislodgment, it is not very sensitive to needle drop-out.

Additional other devices and methods are generally known to monitor vascular access based on the electrical conductivity of blood. For example, Australian Patent No. 730,338 based on PCT Publication No. WO 99/12588 employs an electrical circuit which includes two points through which current is induced in blood flowing through an extracorporeal circuit in a closed loop. Electrical current is induced by means of a coil that is placed around the outside of the tubing of the blood circuit. Thus, each coil does not directly contact the blood as it circulates through the tubing. In this regard, an electrical current is induced in the blood loop by an alternating current that flows through one of the coils. The second coil is then utilized to measure a change in amperage of the induced current as it flows through the blood circuit.

In this regard, electrical current is coupled to a blood treatment system that includes a number of high impedance components, such as a blood pump, air bubble traps, pinch clamps and/or the like. Because of the large impedance of the conducting fluid loop (due to the peristaltic pump and other components), the induction and detection of a patient-safe current requires an impractically complex design of the coil and system. Further, a high level of noise would necessarily result from the use of such levels of induced current. This can adversely impact the sensitivity of detection. If lower currents are used, the field coil would have to be increased in size to detect such low current levels. This may not be practical in use, particularly as applied during dialysis therapy.

PCT Publication No. WO 01/47581 discloses a method and device for monitoring access to the cardiovascular system of a patient. The access monitoring employs an electrical circuit which can generate and detect a current at separate points along a blood circuit connected to the patient. Electrical current is coupled to the blood using capacitive couplers that each have a metal tube placed around the blood circuit tubing. In this regard, the metal tube defines a first plate of a capacitor; the blood circuit tubing defines the dielectric; and the blood inside of the blood circuit tubing defines the second plate of the capacitor.

The generator applies a potential difference between a pair of points to generate a current in a segment of the blood circuit. A detector utilizes an additional and separate pair of contact points to measure the current along at least one section of the venous branch between a first contact point and the venous needle. The change in voltage (dV) can then be determined based on a measured change in current and compared to a reference range (I) to monitor access conditions. In this regard, PCT Publication No. WO 01/47581 requires a complex circuit design that utilizes multiple sets of capacitive couplers to monitor vascular access conditions. This can increase the cost and expense of using same.

Further, the mere use of capacitive coupling to inject an electric signal in the blood circuit and/or for detection purposes can be problematic. In this regard, the signal must pass through the tubing of the blood circuit as the tubing acts as a dielectric of the capacitor. This may cause an excess level of noise and/or other interference with respect to the detection of changes in vascular access conditions.

In this regard, it is believed that known devices, apparatuses, systems, and/or methods that can be used to monitor a patient's access conditions may not be capable of detecting change in access conditions, such as in response to needle drop-out, with sufficient sensitivity and specificity to ensure immediate detection of blood loss such that responsive measures can be taken to minimize blood loss. As applied, if twenty seconds or more of time elapses before blood loss due to, for example, dislodgment of the venous needle, over 100 milliliters in blood loss can occur at a blood flow rate of 400 ml/min, which is typical of dialysis therapy. Thus, the capability to respond quickly upon immediate detection of dislodgment of an access device, such as a needle, from a patient is essential to ensure patient safety.

In addition to dislodgement, additional other parameters are, in general, monitored to evaluate changes thereof during medical procedures including dialysis therapy. For example, temperature sensors, pressure sensors, conductivity sensors and the like are generally known and used in a variety of ways to detect and monitor condition changes during medical therapy.

As applied to dialysis therapy and the like, a dialysis solution can be administered to a patient in mixed form. In this regard, the extent to which the solution is mixed can have an impact on the effectiveness of the associated therapy. In dialysis therapy, the solutions may have varying pH levels that are at levels considered to be non-physiologic prior to mixing, while after mixing, the final solution is required to have a pH at a physiological level necessary for effective and safe administration during therapy. In general, conductivity sensors and pH sensors are known and used. However, it is believed that known sensors may not be as effective in terms of detection capabilities and relative ease of use, particularly as applied during dialysis therapy.

Accordingly, efforts have been directed at designing apparatuses, devices, systems and methods for improved monitoring of patient therapy, such as detecting changes in patient access conditions in response to needle dislodgment, detecting changes in solution compounding and mixing, and the like, wherein detection is sensitive, specific and immediate in response to such changes such that responsive measures can be suitably taken to provide the patient with effective therapy, such as dialysis.

SUMMARY OF THE INVENTION

The present invention provides improved devices, apparatuses, systems and methods that utilize electrically conductive materials to monitor a variety of different conditions or parameter changes associated with the administration of one or more solutions during medical therapy. In turn, this can facilitate the safe and effective administration of the medical therapy, such as dialysis therapy.

In an embodiment, the conductive material includes a polymer conductive material that can include, for example, a polymer conductive component or a polymer matrix and a separate conductive component that is incorporated within the polymer matrix. The conductive materials of the present invention can be utilized in a number of different applications. For example, the conductive materials, such as the conductive polymer material, can be employed to monitor solution mixing and compounding. This can be utilized to evaluate whether the solution or solutions have been effectively mixed prior to administration during therapy. This can be determined by monitoring a pH change in the solution based on changes in conductivity. In this regard, the solution can be derived from a mixture of solution components with varying pH levels, such as between about 1.8 to about 9.2. Thus, the present invention can be utilized to determine whether the pH of the mixed solution is effectively maintained prior to use.

The present invention provides improved devices, apparatuses, systems, and methods for detecting dislodgment or disconnection of an access device, such as dislodgment of a needle inserted in a patient during dialysis therapy. The devices, apparatuses, systems, and methods of the present invention utilize an electrical circuit with a number of electrical contacts which are in fluid contact with the fluid circuit such that an electrical signal can be injected into at least a segment including, for example, a loop defined along at least a portion of the conducting fluid circuit. In this regard, a direct-contact measurement can be used to provide immediate detection of a change in an electrical value in response to a change in access conditions, such as a change in impedance due to dislodgment of a needle or other access device from the patient during medical therapy including, for example, dialysis therapy and medication delivery.

An advantage of the present invention is to provide an improved device, apparatus, system and/or method for monitoring patient therapy, such as for detecting patient access disconnection, for monitoring solution compounding and the like.

Another advantage is to provide devices, apparatuses, systems and methods that employ electrically conductive materials, such as conductive polymer materials, to monitor patient therapy, such as dialysis.

A further advantage of the present invention is to provide an improved device, apparatus, system and/or method for detecting dislodgment of an access device from a patient during medical therapy including dialysis therapy.

Yet another advantage of the present invention is to provide a sensitive, specific and responsive apparatus and/or device for monitoring patient therapy, such as for detecting access disconnection during selfcare and home hemo treatments and for monitoring solution mixing conditions, such as pH changes, prior to use.

Moreover, an advantage of the present invention is to provide a viable device or apparatus for allowing a patient or other non-medical personnel in a non-medical facility to administer a dialysis therapy that uses a portion of the patient's circulatory system.

Furthermore, an advantage of the present invention is to provide an improved device, system and method for monitoring and/or controlling blood loss from a patient.

Yet another advantage of the present invention is an improved device for connecting an electrical contact to a fluid circuit allowing fluid and electrical communication between the electrical contact and fluid flowing through the fluid circuit.

Yet a further advantage of the present invention is to facilitate the safe and effective administration of medical therapy, such as dialysis therapy.

Additional features and advantages of the present invention are described in, and will be apparent from, the following Detailed Description of the Invention and the figures.

BRIEF DESCRIPTION OF THE FIGURES

FIG. 1A illustrates a schematic view of an embodiment of the present invention showing two needles insertable within a patient through which blood flows to and from an extracorporeal system.

FIGS. 5A and 5B illustrate a coupler according to an embodiment of the present invention.

FIGS. 7A and 7B illustrate a sensor assembly according to an embodiment of the present invention.

DETAILED DESCRIPTION OF THE INVENTION

Figure 1B:
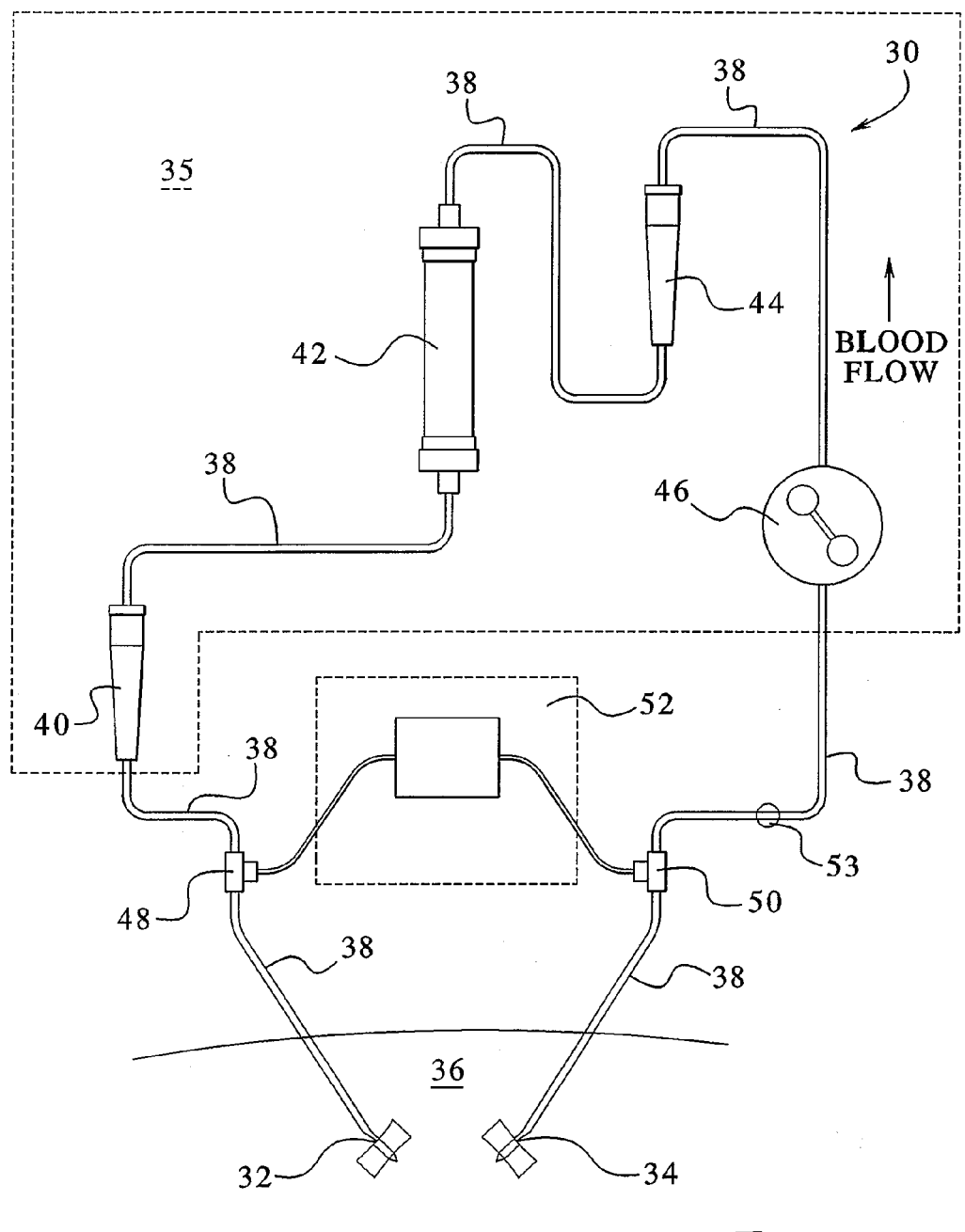
FIG. 1B illustrates a schematic view of an embodiment of the present invention capable of detecting needle dislodgment during dialysis therapy.

The present invention generally relates to electrically conductive materials that can be effectively employed to monitor patient therapy. This can facilitate the safe and effective administration of patient therapy, such as dialysis therapy. In an embodiment, the conductive materials of the present invention include a conductive polymer material as described below in greater detail.

The present invention provides medical devices, apparatuses, systems and methods for detecting access disconnection. More specifically, the present invention provides medical devices, apparatuses, systems, and methods that employ, in part, an electrical circuit with electrical contacts in fluid contact and electrical communication with a fluid circuit allowing a direct conductivity measurement to be used such that dislodgment of a needle or other access device through which fluid flows between a patient and the fluid circuit can be immediately detected. In this regard, fluid loss (i.e., blood loss) due to, for example, dislodgment of a needle from a patient undergoing medical treatment, such as dialysis therapy, medication delivery or the like, can be controllably minimized. In an embodiment, the conductive polymer materials of the present invention can be utilized to monitor solution compounding and mixing to ensure effective administration of the mixed solution during therapy, such as to determine whether a pH level of the mixed solution is effectively maintained prior to use.

It should be appreciated that the present invention is not limited to the detection of needle dislodgment but can be utilized to detect the dislodgment or disconnection of any suitable access device. As used herein, the term "access disconnection" or other like terms means any suitable condition or event which can cause a loss or leak of an electrically conductive fluid flowing along a fluid circuit connected to the patient provided that a change in the electrical continuity between electrical contacts coupled to the fluid circuit can be detected. It should be appreciated that a change in the electrical continuity as measured by an electrical value, such as impedance, may be detected even in the absence of dislodgment of an access device from the patient. The term "access device" as used herein or other like terms means a suitable device that can be inserted within a patient such that fluid, including blood, can pass to, through and/or from the patient via the access device. The access device can include a variety of different and suitable shapes, sizes and material make-up. Examples of an access device includes needles, catheters, cannulas or the like. The access device can be composed of any suitable material including, for example, stainless steel, plastic or like biocompatible materials.

Although in the embodiment set forth below the apparatus and/or device is designed for use in a dialysis therapy, such as hemodialysis, hemofiltration or hemodiafiltration, it should be noted that the present invention can be used in a number of different medical therapies that employ a variety of different and suitable fluid systems, such as extracorporeal blood systems. For example, the invention of the present application can be used during intravenous infusion that can employ the use of a single needle insertable within the patient for delivering a medical solution or drug, blood, blood products, processed blood or the like between the patient and the fluid system. In addition, the present invention can be used in plasma exchange therapies, where a membrane is used to separate whole blood into plasma and cellular components.

With respect to dialysis therapy, the present invention can be used in a variety of different therapies to treat kidney failure. Dialysis therapy as the term or like terms are used throughout the text is meant to include and encompass any and all forms of therapies that utilize the patient's blood to remove waste, toxins and excess water from the patient. Such therapies include both intermittent, including hemodialysis, hemofiltration and hemodiafiltration, and continuous therapies used for continuous renal replacement therapy (CRRT). These continuous therapies include slow continuous ultrafiltration (SCUF), continuous veno-venous hemofiltration (CVVH), continuous veno-hemodialysis (CVVHD), and continuous veno-venous hemodiafiltration (CVVHDF). Dialysis therapy can also include peritoneal dialysis, such a continuous ambulatory peritoneal dialysis, automated peritoneal dialysis and continuous flow peritoneal dialysis. Further, although the present invention, in an embodiment, can be utilized in methods providing a dialysis therapy for patients having chronic kidney failure or disease, it should be appreciated that the present invention can be used for acute dialysis needs, for example, in an emergency room setting. Lastly, as one of skill in the art appreciates, the intermittent forms of therapy (i.e., hemofiltration, hemodialysis and hemodiafiltration) may be used in the in center, self/limited care as well as the home settings.

In an embodiment, the present invention includes an electrical circuit with a number of electrical contacts, preferably a pair of electrical contacts, in fluid contact and electrical communication with the fluid circuit. The electrical contacts can include any suitable device through which electrical connection can be made with the fluid circuit thereby defining a conductive pathway or conductor loop therein. In an embodiment, at least one of the electrical contacts includes a conductive polymer material as described below in greater detail. Changes in an electrical value or any suitable parameter associated with the conductor loop can then be monitored in response to changes in access conditions as described below. In an embodiment, the electrical contact includes an electrode which can be coupled to the fluid circuit such that an electrical connection can be made in fluid contact with fluid flowing through the fluid circuit as discussed below.

For example, a constant current or other suitable electrical signal can be injected into the fluid circuit via an electrode pair in contact with the fluid flowing in between the electrodes thereby defining a loop along at least a portion of the conducting fluid circuit. A change in an electrical value, preferably impedance, can then be measured in response to access disconnection. This can provide a direct conductivity measurement capable of detecting a change in impedance or other suitable electrical parameter of the fluid, such as an electrically conductive fluid including blood, medical solutions or the like, as it flows between a patient and a fluid system (i.e., an extracorporeal blood system) via a needle, needles or other access device(s) inserted within the patient.

In this regard, the present invention can effectively detect dislodgment of a needle (e.g., a venous needle and/or an arterial needle) or other access device through which blood or other suitable fluid can flow, for example, to, through, and from the patient, such as a blood circuit used during dialysis therapy. The detection capability of the present invention is believed to be immediate based on the measurable change in, for example, impedance of the electrically conductive fluid or fluids due to fluid loss resulting from disconnection of the access device from the patient.

The immediate detection capabilities of the present invention are important, particularly as applied to dialysis therapy where a significant amount of blood loss can occur within a relatively short period of time if delays in detection and responsive actions to stop the blood loss occur. Under typical dialysis conditions, if 20 seconds or more time elapses before blood loss due to dislodgment is detected and stopped, over 100 milliliters of blood can be lost based on typical blood flow rates of 400 milliliters/minute.

Applicants have discovered that the present invention can detect access disconnection, particularly in response to venous needle dislodgment during dialysis therapy, with a high degree of sensitivity and specificity in addition to its immediate detection capabilities. The direct-contact measurement of the present invention is capable of detecting a change of an electrical value, preferably impedance, due to needle dislodgment or the like as the blood flows through the blood circuit during dialysis therapy. As used herein, the term "electrical value" or other like terms means any suitable electrical parameter such as, impedance, resistance, voltage, current, rates of change thereof and combinations thereof. The detection of a change in impedance or the like is an indication that the needle has become dislodged or other like condition has occurred. It is noted that the detection capabilities of the present invention can also effectively detect blood loss during medical therapy resulting from a disconnection in the fluid circuit, even if the needle or needles have not become dislodged. In this regard, the present invention can be effectively utilized to controllably minimize blood loss from the patient based on the ability of the present invention to immediately measure a change in impedance or the like due to blood loss with a high degree of sensitivity and specificity. This can facilitate the safe and effective administration of patient therapy as previously discussed.

The devices and apparatuses of the present invention can include a variety of different components and configurations depending on the applied medical therapy such that fluid loss, particularly blood loss due to needle dislodgment or the like, can be effectively monitored.

Multiple Access Disconnection

Referring now to FIG. 1A, an embodiment of the apparatus 10 of the present invention includes a pair of electrical contacts 12 in fluid contact with a blood tubing set 14 of a blood circuit 16. The blood circuit 16 connects a patient 18 to an extracorporeal blood system 20 as applied to, for example, dialysis therapy including hemodialysis, hemofiltration, hemodiafiltration, continuous renal replacement or the like or plasma therapies. The pair of electrical contacts 12 includes a first electrical contact 22 and a second electrical contact 24 which are attached to a respective first tube member 26 and second tube member 28 of the blood circuit 16. The first tube member 26 is connected to a venous needle or other suitable access device inserted into a vascular access region (not shown) of the patient. The second tube member 28 is connected to an arterial needle or the like also inserted into a vascular access region (not shown) of the patient. During dialysis therapy, for example, blood flows from the patient 18 through the arterial needle to the extracorporeal blood system 20 that includes, for example, a dialysis machine, via the second tube member 28 where the blood is treated and delivered to the patient 18 through the venous needle via the first tube member 26.

As the blood flows through the blood circuit during dialysis therapy, a constant electric current or the like generated by a controller 29 can be injected or passed into the flowing blood via the electrical contact pair, preferably an electrode pair as described below. In an embodiment, at least one additional electrode can also be utilized in any suitable manner.

The electrode pair connected to the controller 29 or other suitable electronic device can then be used to measure a voltage change across an unknown fluid (e.g., blood) impedance or other like electrical value to detect a change in impedance or the like across the vascular access region. In an embodiment, one electrode can be used to inject the electrical signal into the fluid circuit while the other electrode of the pair can be used to sense a change in the electrical value and pass an electrical signal indicative of the same to the controller for processing and detection purposes. Upon dislodgment of at least one of the venous needle and arterial needle from the blood circuit or other suitable condition, an immediate and detectable increase in impedance or the like can be measured as compared to the impedance or other suitable parameter measured under normal operating conditions.

It should be appreciated that the present invention as embodied in FIG. 1A can be modified in a variety of suitable ways depending on the medical therapy as applied. For example, the venous and arterial needles can be inserted into the vascular access of the patient on any suitable part of the patient's body, such as the upper arm, lower arm, upper thigh area or the like during dialysis therapy. As previously discussed, the present invention can be applied to a variety of different medical therapies including intravenous infusions, plasma exchanges, medication delivery, drug delivery, blood delivery and dialysis therapies (i.e., hemofiltration, hemodialysis, hemodiafiltration and continuous renal replacement).

As illustrated in FIG. 1B, an embodiment of an apparatus 30 of the present invention is shown as applied during dialysis therapy. In an embodiment, the present invention includes a venous needle 32 and arterial needle 34 inserted within a patient access 36. The venous needle 32 and arterial needle 34 are connected to the dialysis system 35 via a number of tube members 38 that connect the various components of the dialysis system 35 including, for example, a venous drip chamber 40, a dialyzer 42, an arterial drip chamber 44 and a blood pump 46. It should be appreciated that one or more of the components of the dialysis system can be provided within a dialysis machine coupled to the blood circuit. As shown in FIG. 1B, a first electrical contact coupling device 48 and a second electrical contact coupling device 50 are positioned between the dialysis system 35 and the venous needle 32 and the arterial needle 34. As used herein, the term "electrical contact coupling device," "coupling device" or other like terms means any suitable device that can be used to connect an electrical contact to the fluid circuit. In an embodiment, the electrical contact coupling device can be used to contact the electric contact to the fluid circuit allowing fluid contact and electrical connection with the fluid flowing through the fluid circuit as described below.

In an embodiment, the electrical contact pair, preferably an electrode pair, is connected to a controller 52 or other suitable electronic device. The controller can be used to inject an electric signal via the electrode pair and into the blood and/or other fluid as it flows through the blood circuit. This provides a conductor loop along which changes in electrical parameters or values can be measured. The controller 52 which is coupled to the electrode pair can also be used to measure this change. It should be appreciated that the controller can include a single electronic device or any suitable number of devices in electrical connection with the electrical contacts to input an electrical signal into the blood circuit thereby defining a conductor loop, to measure a change in an electrical parameter or value associated with the conductor loop and/or perform any other suitable tasks, such as processing the detectable signal as discussed below.

Preferably, the electrical signal is generated from a constant current that is supplied to the electrodes until dislodgment occurs. The voltage across an unknown impedance of the fluid (e.g., blood) circulating through the blood circuit can then be measured (not shown) to detect a change in impedance due to changes in access conditions. However, it should be appreciated that any suitable electrical parameter and changes thereof can be monitored to detect needle drop-out or the like as previously discussed.

As demonstrated below, the detection capabilities of the present invention are highly sensitive, specific and virtually immediate in response to access disconnection, such as needle dislodgment. Further, the electronic circuit of the present invention is relatively simple in design such that preferably one electrode pair is necessary to conduct direct conductivity measurement. This can reduce costs and effort as compared to known vascular access monitoring techniques that only employ non-invasive detection techniques, such as, capacitive couplers and induction coils as previously discussed.

Applicants have discovered that the total impedance measured ("Z") can be modeled as two lumped impedances in parallel with one impedance ("$Z_D$") being produced by the pump segment, the dialyzer, the drip chambers and/or other suitable components of the dialysis system and/or the like. The other impedance component ("$Z_P$") is formed by the patient's vascular access and associated tubing which carries blood to and from the vascular access and/or the like. In this regard, the total impedance measured can be characterized as a function of both $Z_D$ and $Z_P$ as follows:

$$Z=(1/Z_D+1/Z_P)^{-1}$$

Despite this parallel impedance, Applicants have discovered that the electrical contacts in connection with the controller can be used to measure a change in impedance along the conductor loop as blood flows through the blood circuit in response to access disconnection, such as needle dislodgment. If needle dislodgment occurs, the conductor loop along at least a portion of the fluid circuit changes from a closed circuit to an open circuit and thus $Z=Z_D$ where $Z_P$ approaches infinity. In this regard, the direct conductive measurement capabilities of the present invention can be effectively used to detect access disconnection.

Applicants note that the $Z_D$ component can produce a level of electrical interference associated with the time-varying high impedance of the components of a medical system coupled to the fluid circuit, such as a dialysis system and its components including, for example, a blood pump, a drip chamber and/or the like. Applicants have discovered that the interference due to the $Z_D$ component can be effectively eliminated, or at least reduced, if necessary. In an embodiment, the signal associated with the detection of Z or the like can be further processed as discussed below. Alternatively, in an embodiment, the electrical circuit of the present invention can be designed to block or bypass one or more components of the dialysis system from the conductor loop or pathway defined along the blood circuit as described below. In this regard, the accuracy, sensitivity and responsiveness with respect to the detection of access disconnection can be enhanced.

In an embodiment, a third electrical contact point 53 can be utilized to minimize or effectively eliminate the interferences with respect to the high impedance components coupled to the blood circuit, such as the blood pump and the like. The additional contact point can be made in any suitable way. For example, the third contact point can be an electrode or other suitable device through which electrical continuity can be established between it and one of the electrodes of the coupling devices. In an embodiment, the third electrical contact can be attached to a fluid circuit in fluid and electrical communication with fluid flowing through same.

The third contact point 53 can be positioned at any suitable position along the blood circuit. Preferably, the third contact point 53 is positioned at any suitable location between the blood pump 46 and the coupling device 50 as shown in FIG. 1B. An equalization potential can then be applied between the third contact point 53 and the electrode of the coupling device 50. The potential is applied at a voltage that is equal to the potential applied between the electrodes of the first coupling device 48 and the second coupling device 50.

This effectively causes the electric current or the like, once injected into the blood circuit, to bypass one or more of the components of the dialysis system. In an embodiment, the third contact point 53 can be positioned such that the electric current or the like would effectively bypass all of the components of the dialysis system as shown in FIG. 1B.

Single Access Disconnection

Figure 1C:
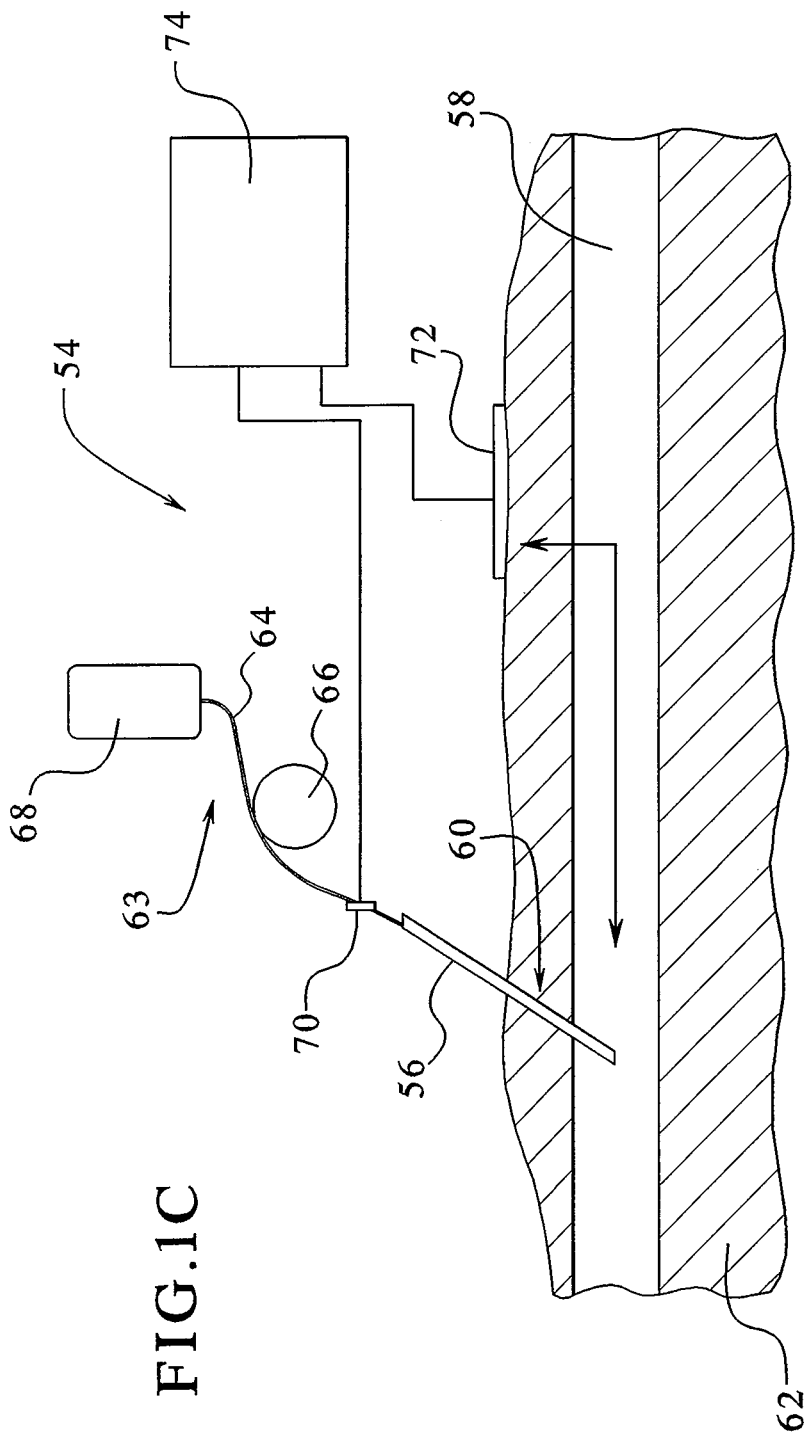
FIG. 1C illustrates a perspective view of an embodiment of the present invention showing access disconnection detection capabilities during medical therapies administered via a single needle.

The electrical contacts of the present invention can be positioned in any suitable location relative to the needle, needles or suitable access device inserted within the patient. As illustrated in FIG. 1C, an embodiment of the present invention as applied with respect to the detection of access detection, such as the dislodgment of a single access device inserted within the patient is shown. This type of application is applicable to a variety of different and suitable medical therapies administered via a single access device, such as a single needle, including intravenous infusion and dialysis therapy including hemodialysis, hemofiltration, hemodiafiltration and continuous renal replacement.

As applied, an electrically conductive fluid, such as blood, a blood product, a medical fluid or the like flows between the patient and a fluid system via a single access device. Dislodgment detection of a single access device can include, for example, the detection of needle dislodgment during the delivery of any suitable and electrically conductive fluid or fluids including, for example, blood or medical drug or solution (i.e., a medication contained in an electrically conductive fluid, such as saline), processed blood, blood products, intravenous solutions, the like or combinations thereof. The fluid delivery can be made between a suitable container, such as blood bags or like fluid delivery devices, and a patient. In this regard, immediate and responsive detection of access disconnection via the present invention can be effectively utilized to monitor and control the transfer of blood or a medical fluid, such as a medication or drug, during medical therapy administered via a single needle.

As shown in FIG. 1C, an embodiment of the apparatus or device 54 of the present invention includes an access device 56; such as a needle, inserted into a blood vessel 58 within a needle insertion site 60 of the patient 62. The needle 56 is connected to the fluid system 63, such as a fluid infusion system, via a tube member 64. The infusion system includes, for example, an infusion pump 66 for transferring the blood or the like from a container 68 (e.g., blood bag) to the patient. A first electrical contact 70 is spaced apart from the needle 56 along the tube member 64 and a second electrical contact 72 is attached to the patient near the insertion site 60. The first electrical contact 70 is in fluid contact with the fluid as it flows from the delivery container 68 to the patient.

In this configuration, the first and second electrical contacts, preferably electrodes, can be used to monitor changes in an electrical value, preferably impedance, within a conductor loop formed by at least a portion of the fluid circuit as an electric signal passes therein. In an embodiment, at least one of the electrical contacts can include a conductive polymer material as described below in greater detail. The electrical contact points can be coupled to an electronic device 74 which is capable of processing a detectable signal transmitted through the electrodes in response to a change in impedance or the like due to dislodgment of the single access device as described in detail below. Preferably, the electrical signal is generated by a constant current supplied to the electrodes such that a direct conductivity measurement can be conducted to detect a change in impedance or the like in response to changes in vascular access conditions, such as dislodgment of the access needle.

It is believed that the measured impedance, in the single needle application, is a function of both the impedance of the fluid (i.e., blood) and the impedance as measured across the insertion site. In this regard, the electronic device 74 can be adjusted to detect the impedance at the level equivalent to the combined impedance of all items of the electrical path (i.e., the conductive fluid in the tube, needle, blood stream of venous vessel, body tissue, impedance across the skin with respect to the sensing electrode 72 and the like).

Electrical Contacts

As previously discussed, the electrical contacts of the present invention are in fluid contact with the fluid as it flows through the fluid circuit. In this regard, the electrical contacts can be utilized to monitor changes in conditions associated with patient therapy. For example, the electrical contacts allow for a direct conductivity measurement which is capable of immediately detecting, with high sensitivity and specificity, a change (e.g., an increase) in impedance or the like due to access disconnection, such as dislodgment of a venous needle (arterial needle or both) from the blood circuit during dialysis therapy. Other types of monitoring applications include monitoring conductivity changes in response to solution compounding as described below in greater detail. It should be appreciated that the present invention can be utilized to monitor one or a combination of condition changes.

The electrical contacts can be composed of any suitable conductive and biocompatible material, such as, any suitable electrode material including stainless steel, other suitable conductive materials or combinations thereof. It is essential that the electrode material is biocompatible. In an embodiment, the electrical contact includes a conductive polymer material as described below in greater detail.

It should be appreciated that the electrical contacts can be constructed in a variety of different shapes and sizes, illustrative examples of which are described below. For example, the electrical contacts can be configured or designed as a plaster electrode which includes an agent capable of expanding when in contact with moisture. The agent can include a variety of suitable materials including gels that are known to expand more than ten times in volume upon contact with moisture.

In an embodiment, the plaster electrode can be utilized to detect fluid (i.e., blood leakage) at an insertion site of an access device insertable within a patient during the administration of medical therapy via a single access device as previously discussed. Upon contact with the fluid, the plaster electrode would necessarily expand to such an extent that the electrode contact is broken, thus causing a detectable increase in impedance of the fluid as it flows from the fluid system to the patient via the needle.

In an embodiment, one or more electrodes (not shown), such as one or more plaster electrodes as previously discussed, can be used in combination with the electrical contact pair as shown, for example, in FIGS. 1A and 1B. For example, a plaster electrode can be attached to the patient near the insertion site of either or both of the arterial and venous needles. In this regard, the plaster electrode(s) can be utilized to detect leakage of fluid, such as blood, from the insertion site of the access device(s).

In an embodiment, an electrode pair is coupled to the blood circuit in an invasive manner (illustrated in FIGS. 2A-2C as discussed below) such that the electrodes contact the blood as previously discussed. An excitation source that includes a constant current source or the like can be applied to the electrodes to inject an electric signal into the blood circuit thereby defining a conductor loop along which direct conductivity measurements can be performed.

To ensure patient safety, the excitation source is typically isolated from the instrument power. Preferably, the excitation source produces a constant electrical current that passes through the blood via the electrodes. Any suitable amount of current can be generated for detection purposes. In an embodiment, the electrical current as it passes through the blood is maintained at a level of about 10 microamperes or less, preferably about 5 microamperes or less. It should be appreciated that the present invention can be operated at low levels of current (e.g., 10 microamperes or less) such that the level of current has negligible, if any, effect on the health and safety of the patient.

It should be appreciated that the impedance or other suitable parameter can be measured and calculated in a variety of different and suitable ways. For example, the amplitude, phase and/or frequency of the constant current excitation source can be measured and varied during the detection of a change in impedance. Impedance levels can then be detected by measuring the voltage across the electrodes In this regard, the amplitude, frequency and/or phase of the voltage can then be measured and utilized in combination with the measured amplitude, frequency and/or phase of the excitation source to calculate blood impedance levels based on derivations or equations which are typically used to calculate impedance.

The electrical contacts can be connected to the blood circuit in a variety of different and suitable ways. For example, the electrical contacts can be an integral component of the extracorporeal system, a disposable component that can be connected and released from the tubing members of the blood circuit, a reusable component that can be autoclaved between uses, or the like.

Electrical Contact Coupling Device

In an embodiment, the apparatus of the present invention includes an electrical contact coupling device that can be utilized to secure the electrical contacts, preferably electrodes, to the blood circuit such that the electrodes effectively contact the blood and, thus, can be used to effectively monitor changes in access conditions as previously discussed. In an embodiment, at least one of the electrical contacts includes a conductive polymer material as described below. The coupling device of the present invention can also be designed to facilitate the protection of the user against contact with potential electrical sources. In an embodiment, the device can include a conductive element connected to a tube, through which a medical fluid can flow wherein the conductive element has a first portion exposed to the medical fluid, such as blood, and a second portion external to the tube.

The coupling device of the present invention can include a variety of different and suitable configurations, components, material make-up or the like. In an embodiment, the present invention can include a device for connecting an electrical contact to a fluid conduit providing fluid and electrical communication between the electrical contact and fluid flowing through the fluid conduit. The device can include a first member including an annular portion capable of accommodating the electrical contact and a first stem portion connected to the annular member wherein the stem portion has an opening extending therethrough to the annular portion; a second member including a base portion with a groove region and a second stem portion with an opening extending therethrough to the groove region allowing the first member to be inserted and secured to the second member; and a contact member adapted to fit the first and second stem portions allowing the contact member to abut against at least a portion of the electrical contact member allowing an electrical connection to be made between the electrical contact and the contact member. Illustrative examples of the electrical contact coupling device of the present invention are described below.

Figure 2A:
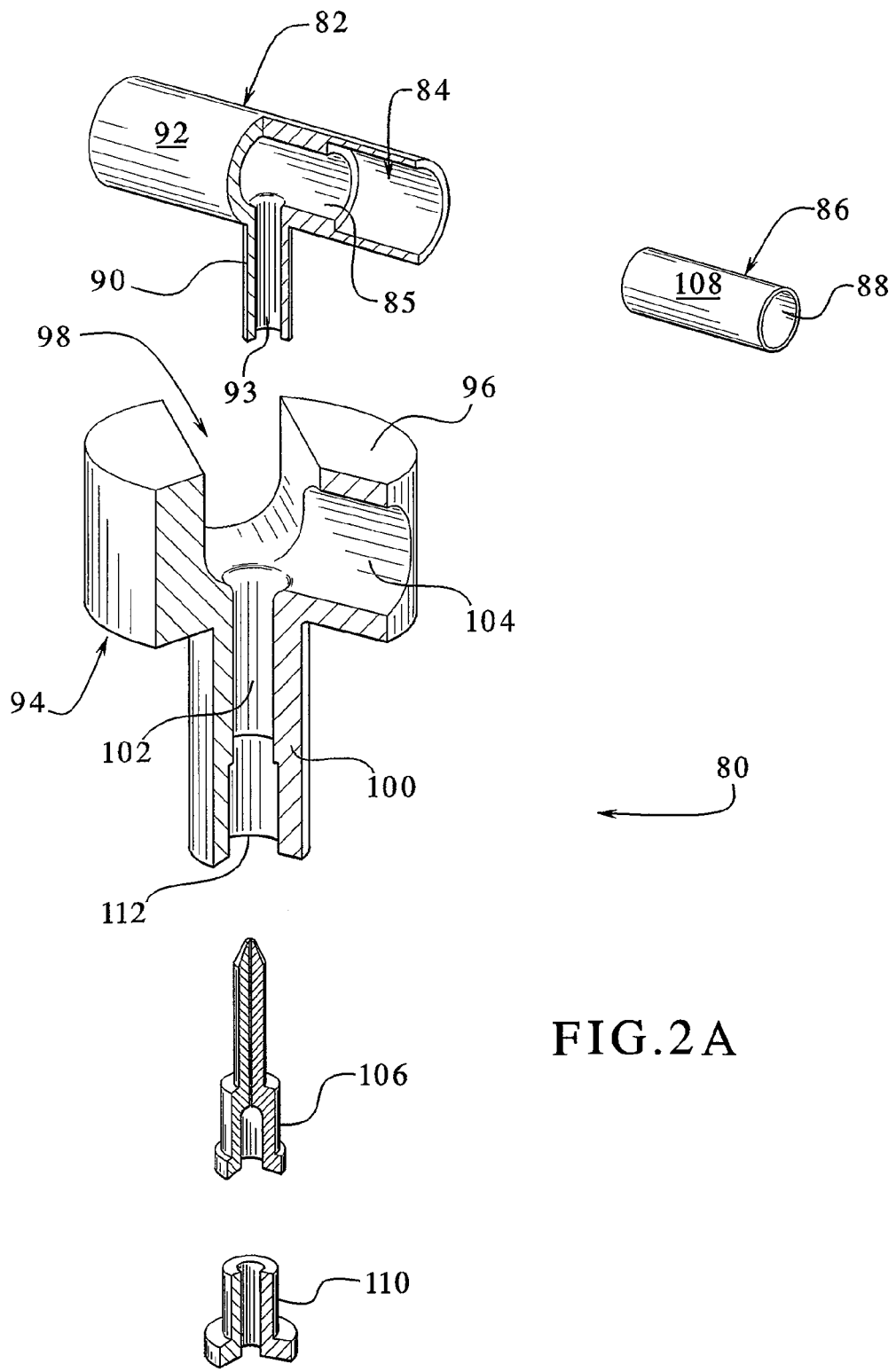
FIG. 2A illustrates an exploded view of an electrical contact coupling device in an embodiment of the present invention.
Figure 2B:
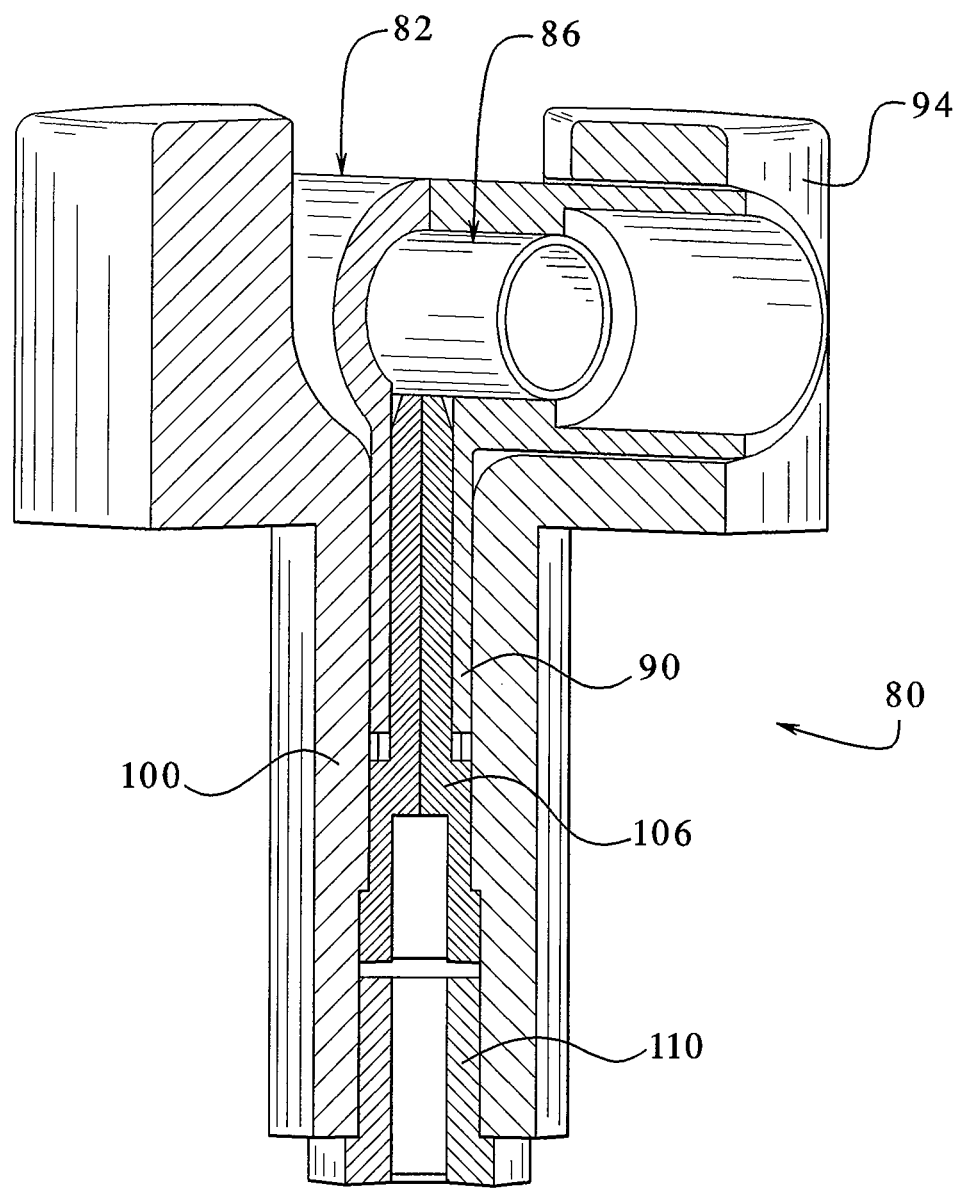
FIG. 2B illustrates a side sectional view of the coupling device of FIG. 2A in an embodiment of the present invention.

As illustrated in FIGS. 2A and 2B, the electrical contact coupling device 80 includes a probe member 82 that has a cylindrical shape with an opening 84 extending therethrough. In this regard, an electrical contact, preferably an electrode 86 having a cylindrical shape can be inserted into the opening 84 such that the electrode 86 is secure within the probe member 82. In an embodiment, the probe member 82 has a channel 85 extending along at least a portion of the opening 84 within which the electrode 86 can be inserted into the probe member 82. A tube member, for example, from a blood tubing set, connector tube member of a dialysis machine or the like, can be inserted into both ends of the opening 84 of the probe member 82 in contact with an outer portion of the channel 85 allowing blood or other suitable fluid to make fluid contact with the electrode 86 in any suitable manner. The electrode 86 has an opening 88 that extends therethrough within which blood (not shown) or other suitable fluid from the fluid circuit can flow. In an embodiment, the diameter of the opening 88 of the electrode 86 is sized to allow blood flow through the electrode 86 such that blood flow levels under typical operating conditions, such as during dialysis therapy, can be suitably maintained. In this regard, the coupling device of the present invention can be readily and effectively attached to a fluid circuit, including a blood circuit or the like, for use during medical therapy including, for example, dialysis therapy. It should be appreciated that the coupling device 80 of the present invention can be attached to the fluid circuit in any suitable way such that electrical and fluid connection can be made with the fluid flowing through the fluid circuit.

The probe member 82 also includes a stem portion 90 that extends from a surface 92 of its cylindrical-shaped body. The stem portion 90 has an opening 93 that extends therethrough. In an embodiment, the stem portion 90 is positioned such that at least a portion of the electrode 86 is in contact with the opening 93 of the stem portion 90.

In order to secure the electrode 86 to the blood circuit, the coupling device 80 includes a socket member 94 that includes a body portion 96 with an opening 98 for accepting the probe member 82 and for accepting a blood tube member (not shown) of the blood circuit such that blood directly contacts the electrode as it circulates through the blood circuit during dialysis therapy. In an embodiment, the socket member 94 includes a stem portion 100 extending from the body member 96 wherein the stem portion 100 includes an opening 102 extending therethrough. As the probe member 82 is inserted through the opening 98 of the body member 96, the stem portion 90 of the probe member 82 can be inserted into the opening 102 of the stem portion 100 of the body 96 of the socket member 94.

In an embodiment, the socket member 94 includes a groove region 104 extending along at least a portion of the body 96 of the socket member 94. In this regard, the probe member 82 can be inserted through the opening 98 and then moved or positioned into the groove region 104 to secure the probe member 82 within the body 96 of the socket member 94.

In an embodiment, the coupling device 80 includes an electrical contact member 106 that is inserted within the opening 102 of the stem portion 100 of the body 96 of the socket member 94 such that the electrical contact member 106 extends through the opening 93 of the stem portion 90 of the probe member 82 to contact at least a portion of a surface 108 of the electrode 86.

The electrical contact member 106 is utilized to connect the electronics (not shown) of, for example, the excitation source, a signal processing device, other like electronic devices suitable for use in monitoring and/or controlling changes in access conditions, such as needle dislodgment. The electrical contact member 106 can be made of any suitable material, such as any suitable conductive material including, stainless steel, other like conductive materials or combinations thereof. In order to secure the electrical contact member 106 in place, a contact retainer member 110 is inserted within the opening 102 of the stem portion 100 at an end region 112 thereof.

In an embodiment, the coupling device is mounted to a dialysis machine, device or system in any suitable manner. For example, the coupling device can be mounted as an integral component of the dialysis machine. As well, the coupling device can be mounted as a separate and/or stand alone component which can interface with any of the components of the apparatus and system of the present invention. In an embodiment, the coupling device 80 can be insertably mounted via the stem portion 100 of the socket member 94 to a dialysis machine or other suitable components.

Figure 2C:
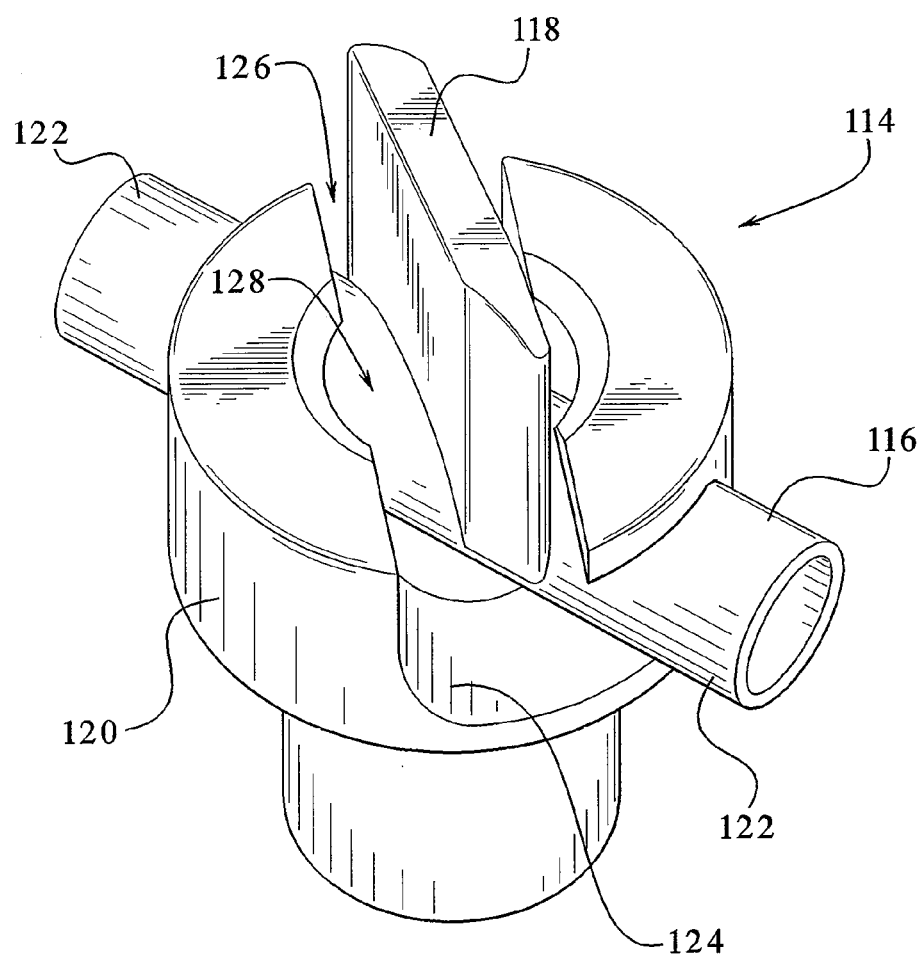
FIG. 2C illustrates another embodiment of the coupling device of the present invention.

It should be appreciated that the electrical contact coupling device can include a variety of different and suitable shapes, sizes and material components. For example, another embodiment of the coupling device is illustrated in FIG. 2C. The coupling device 114 in FIG. 2C is similar in construction to the coupling device as shown in FIGS. 2A and 2B. In this regard, the coupling device 114 of FIG. 2C can include, for example, a cylindrical-shaped electrode or other suitable electrical contact, a probe member for accepting the electrode and securing it in place within a socket member of the sensing device. The probe member includes a stem portion that is insertable within a stem portion of the socket member. An electrical contact member is insertable within the stem portion such that it can contact the electrode. The coupling device of FIG. 2C can also include a contact retainer member to hold the electrical contact member in place similar to the coupling device as shown in FIGS. 2A and 2B.

As shown in FIG. 2C, the probe member 116 of the electrical contact coupling device 114 includes a handle 118 which can facilitate securing the probe member 116 within the socket member 120. The handle 118, as shown, has a solid shape which can facilitate the use and manufacture of the coupling device 114. In addition, the stem portion (not shown) of the probe member 116 is larger in diameter than the stem portion of the probe member as illustrated in FIG. 2A. By increasing the stem size, the probe member can be more easily and readily inserted within the socket member. Further, the probe member is greater in length as compared to the probe member as shown in FIGS. 2A and 2B such that the end regions 122 of the probe member 116 extend beyond a groove region 124 of the socket member 120. This can facilitate securing the probe member within the groove region 124 of the socket member 120.

In an embodiment, an opening 126 of the socket member 120 can include an additional opening portion 128 to accommodate the insertion of the stem portion of the probe member 116, having an increased size, therethrough. This can ensure proper alignment of the probe member with respect to the socket member before insertion of the probe member into the socket member thus facilitating the insertion process.

It should be appreciated that the probe member, socket member and contact retainer member can be composed of a variety of different and suitable materials including, for example, plastics, molded plastics, like materials or combinations thereof. The various components of the coupling device, such as the probe member, socket member and contact retainer member, can be fitted in any suitable way. For example, the components can be fitted in smooth engagement (as shown in FIGS. 2A and 2B), in threaded engagement (as shown in FIGS. 2D and 2E) and/or any suitable fitting engagement or arrangement to one another.

Figure 2D:
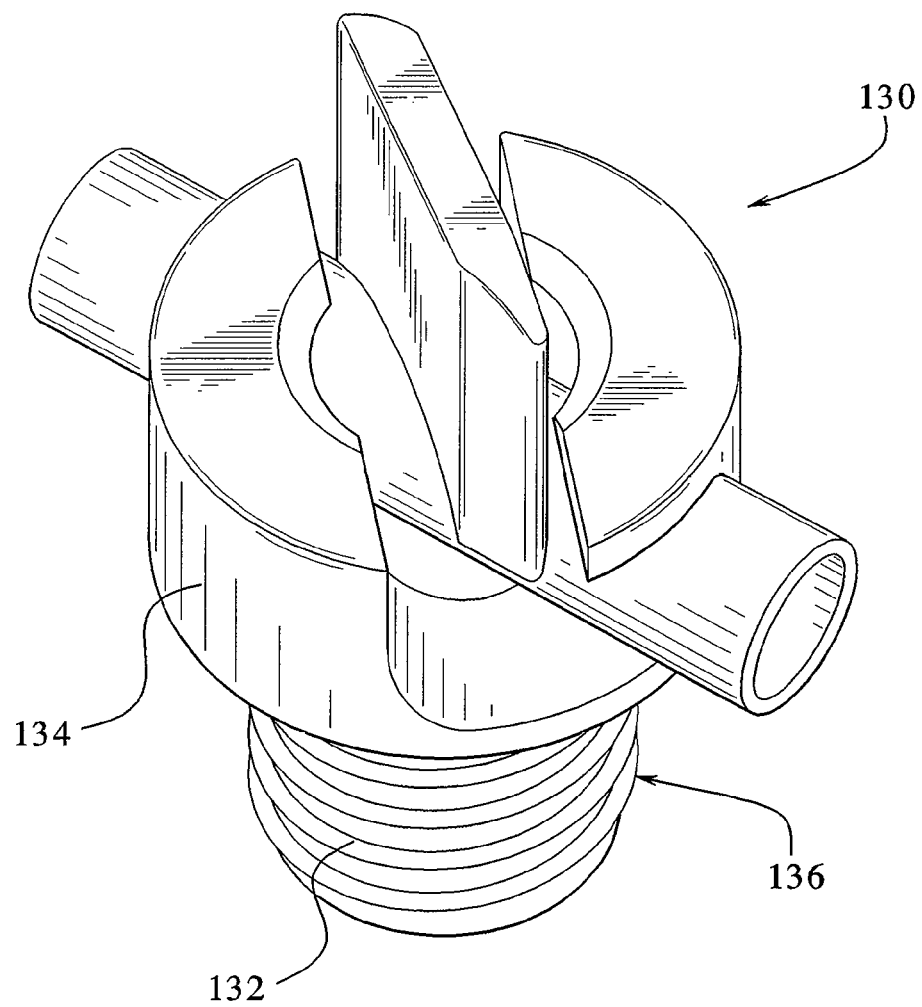
FIG. 2D illustrates another embodiment of the coupling device of the present invention showing a threaded engagement between the components of same.
Figure 2E:
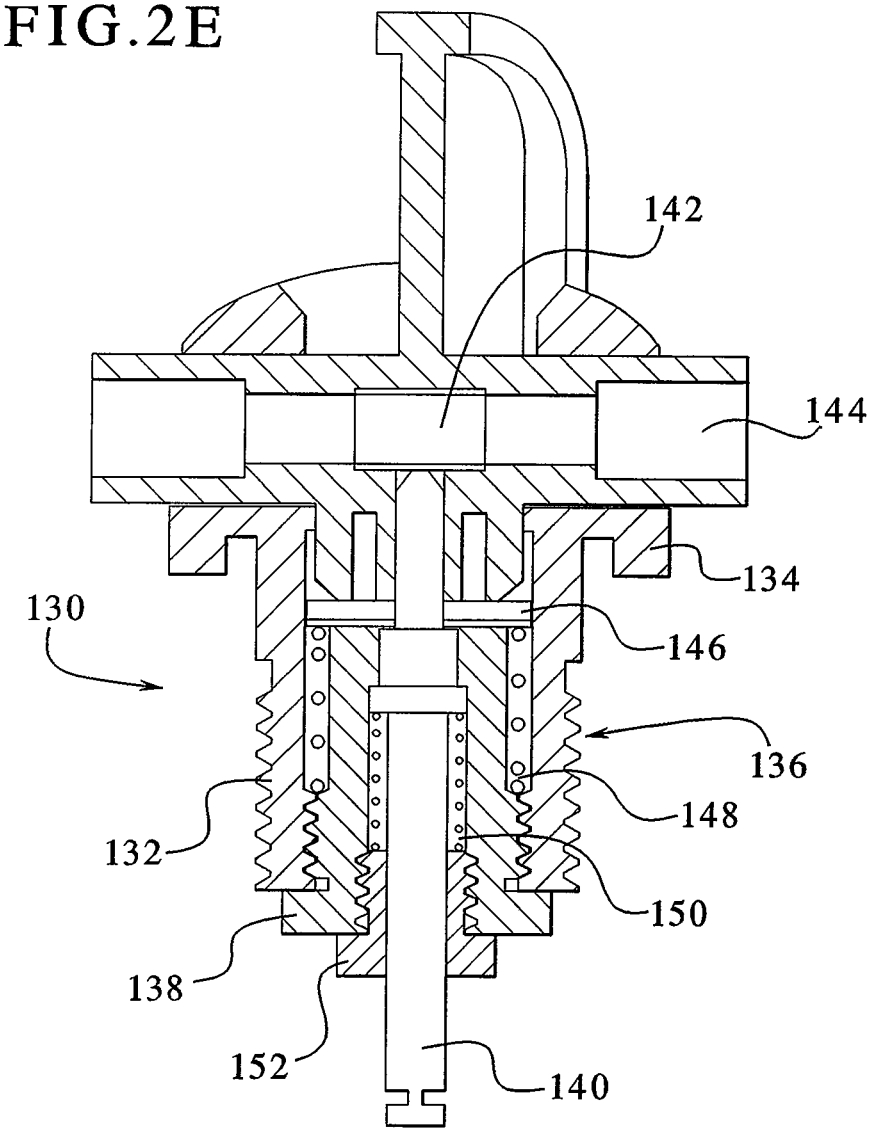
FIG. 2E illustrates a sectional view of FIG. 2D.

As shown in FIGS. 2D and 2E, the coupling device 130 of the present invention can be made of threaded parts which are removably connected to one another to form the coupling device. The threaded parts can facilitate securing the electrode to the blood circuit as well as general use of same as described below.

In an embodiment, the stem portion 132 of the body 134 of the coupling device 130 has a threaded region 136 which can be insertably attached to a dialysis machine or other suitable mounting device in threaded engagement. This can facilitate the ease in which the coupling device is attached and detached from the mounting device.

As shown in FIG. 2E, the stem portion 132 is threaded on both sides allowing it to be in threaded engagement with an annular member 138. The annular member 138 provides direction and support allowing the electrical contact member 140 to abut against the electrode 142 housed in the probe member 144 as previously discussed.

In an embodiment, a plate member 146 made of any suitable conductive material can be depressed against a spring 148 as the probe member 144 is secured to the body 134. At the same time, another spring 150 can be displaced against the electrical contact member 140 in contact with the retainer 152 which is inserted within an annular region of the annular member 138 to secure the electrical contact member 140 to the body 134.

The spring mechanism in an embodiment of the present invention allows the parts of the coupling device 130 to remain in secure engagement during use. It can also facilitate use during detachment of the parts for cleaning, maintenance or other suitable purpose.

As previously discussed, the present invention can be effectively utilized to detect dislodgment of an access device, such as a needle, inserted within a patient through which fluid can pass between the patient and a fluid delivery and/or treatment system. The present invention can be applied in a number of different applications, such as medical therapies or treatments, particularly dialysis therapies. In dialysis therapies, access devices, such as needles, are inserted into a patient's arteries and veins to connect blood flow to and from the dialysis machine.

Under these circumstances, if the needle becomes dislodged or separated from the blood circuit, particularly the venous needle, the amount of blood loss from the patient can be significant and immediate. In this regard, the present invention can be utilized to controllably and effectively minimize blood loss from a patient due to dislodgment of the access device, such as during dialysis therapy including hemodialysis, hemofiltration, hemodiafiltration and continuous renal replacement.

Signal Detection and Processing

As previously discussed, the electrical contacts in connection with the controller can be used to detect a change in impedance or the like in response to needle drop-out or other like changes in access conditions. The electrical contacts can include a variety of suitable conductive materials, such as conductive polymer materials as described below. In an embodiment, the present invention can be adapted to correct for any variations in the baseline impedance over time. This can increase the level of sensitivity with respect to the detection capabilities of the present invention. In this regard, if changes in the baseline impedance are too great and not adequately corrected for, changes in impedance due to needle dislodgment may not be as readily, if at all, detectable above baseline values.

From a practical standpoint, there are a number of different process conditions that may influence a change in the baseline impedance over time. For example, a gradual drift or change in the baseline can occur due to a change in the characteristics, such as the hematocrit, plasma protein, blood/water conductivity and/or the like, of the blood or other suitable fluid during treatment. This can arise due to changes in the level of electrolytes or other components during dialysis therapy.

Figure 3:
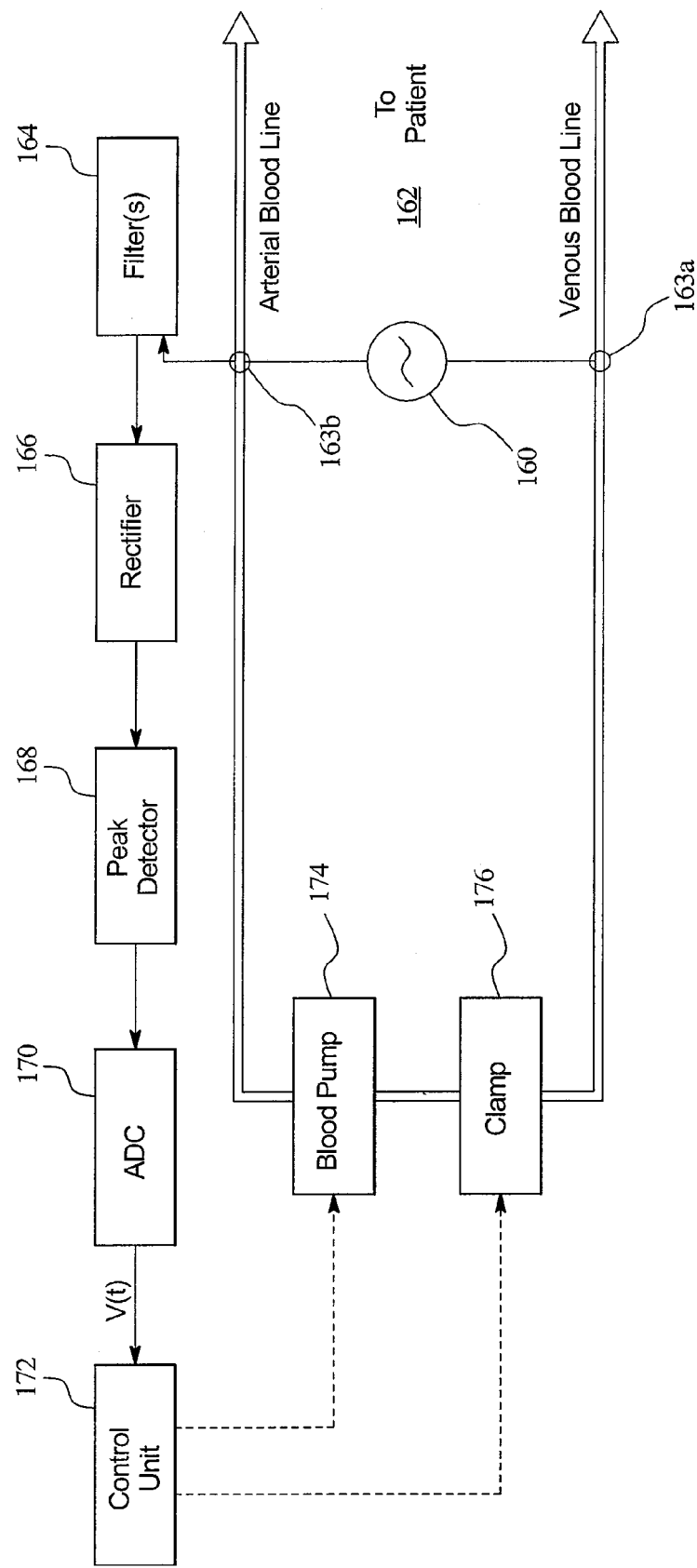
FIG. 3 schematically illustrates an embodiment of the present invention relating to processing of a measurable voltage signal to correct for changes in baseline impedance during treatment.

As illustrated in FIG. 3, the present invention can process a measurable voltage signal to correct for changes in baseline impedance over time. This can enhance the detection capabilities of the present invention as previously discussed. In an embodiment, a current source 160 or the like generates an electric current to pass through the blood as it circulates into, through and out of the patient along the extracorporeal blood circuit 162 which connects the patient via venous and arterial needles to the dialysis system including a variety of process components. The electric current is injected into the blood circuit via a first electrical contact 163a thereby defining a conductor loop or pathway along the blood circuits. Preferably, the current is maintained at a constant level until dislodgment occurs. The second electrode 163b is used to sense voltage or the like along the conductor loop and then pass a signal indicative of same and/or changes thereof to an electronic device for detection and processing as previously discussed. The voltage signal can be measured and processed in any suitable manner.

In an embodiment, the signal is passed through a series of components including a filter or filters 164 which can act to filter noise from the signal, particularly noise derived from the rotation from the pump in order to minimize a false negative and/or positive detection of needle dislodgment, a rectifier 166, a peak detector 168 and an analog to digital converter ("ADC") 170 to digitize the signal. In this regard, the digital signal can then be stored in a computer device (not shown) for further processing. The voltage signal is continually measured and processed over time. With each measurement, the digitized signals are compared to evaluate changes due to baseline changes associated with variations in process conditions over time, such as a change in the characteristics of blood as previously discussed. If a baseline change is determined, the digitized signal can be further processed to correct for the change in baseline.

The voltage data is continually sent to a control unit 172 coupled to the ADC. The control unit continually performs a calculation to determine whether a change in impedance or the like in response to needle dislodgment has occurred. In an embodiment, dislodgment of an access device is detected when $[V(t)-V(t-T)]>C1$, where t is time, where T is the period of blood pump revolution, where C1 is a constant and where $V(t)=I_o*Z$, where $I_o$ is current and where Z is the impedance of the bloodline which is a function of the impedance associated with patient's vascular access and the impedance associated with various components of the dialysis system, such as the dialyzer, as previously discussed.

If disconnection of the patient from the blood circuit is detected, the control unit 172 can be utilized to process the signal in order to minimize blood loss from the patient. In an embodiment, the controller is in communication with a dialysis system as applied to administer dialysis therapy including, for example, hemodialysis, hemofiltration, hemodiafiltration and continuous renal replacement. This communication can be either hard-wired (i.e., electrical communication cable), a wireless communication (i.e., wireless RF interface), a pneumatic interface or the like. In this regard, the controller can process the signal to communicate with the dialysis system or device to shut off or stop the blood pump 174 associated with the hemodialysis machine and thus effectively minimize the amount of blood loss from the patient due to needle dislodgment during hemodialysis.

The controller can communicate with the dialysis system in a variety of other ways. For example, the controller and hemodialysis machine can communicate to activate a venous line clamp 176 for preventing further blood flow via the venous needle thus minimizing blood loss to the patient. In an embodiment, the venous line clamp is activated by the controller and attached to or positioned relative to the venous needle such that it can clamp off the venous line in close proximity to the needle. Once clamped, the dialysis system is capable of sensing an increase in pressure and can be programmed to shut-off the blood pump upon sensing pressure within the blood flow line which is above a predetermined level. Alternatively, the venous line clamp can be controllably attached to the dialysis system.

In an embodiment, an alarm can be activated upon detection of blood loss due to, for example, needle dislodgment during dialysis therapy. Once activated, the alarm (i.e., audio and/or visual or the like) is capable of alerting the patient, a medical care provider (i.e., doctor, registered nurse or the like) and/or a non-medical care provider (i.e., family member, friend or the like) of the blood loss due to, for example, needle dislodgment. The alarm function is particularly desirable during dialysis therapy in a non-medical facility, such as in a home setting or self care setting where dialysis therapy is typically administered by the patient and/or a non-medical care provider in a non-medical setting or environment excluding a hospital or other like medical facility.

In this regard, the alarm activation allows, for example, the patient to responsively act to ensure that the dialysis therapy is terminated by, for example, to check that the blood pump has been automatically shut off to minimize blood loss to the patient. Thus, the patient has the ability to act without the assistance of a third party (i.e., to act on his or her own) to ensure that responsive measures are taken to minimize blood loss. The alarm can thus function to ensure the patient's safety during the administration of dialysis therapy, particularly as applied to home hemo treatments where at least a portion of the dialysis therapy can be administered while the patient is sleeping.

Dialysis Machine

As previously discussed, the present invention can be adapted for use with any suitable fluid delivery system, treatment system or the like. In an embodiment, the present invention is adapted for use with a dialysis machine to detect access disconnection as blood flows between the patient and the dialysis machine along a blood circuit during treatment, including, for example hemodialysis, hemofiltration and hemodiafiltration.

Figure 4A:
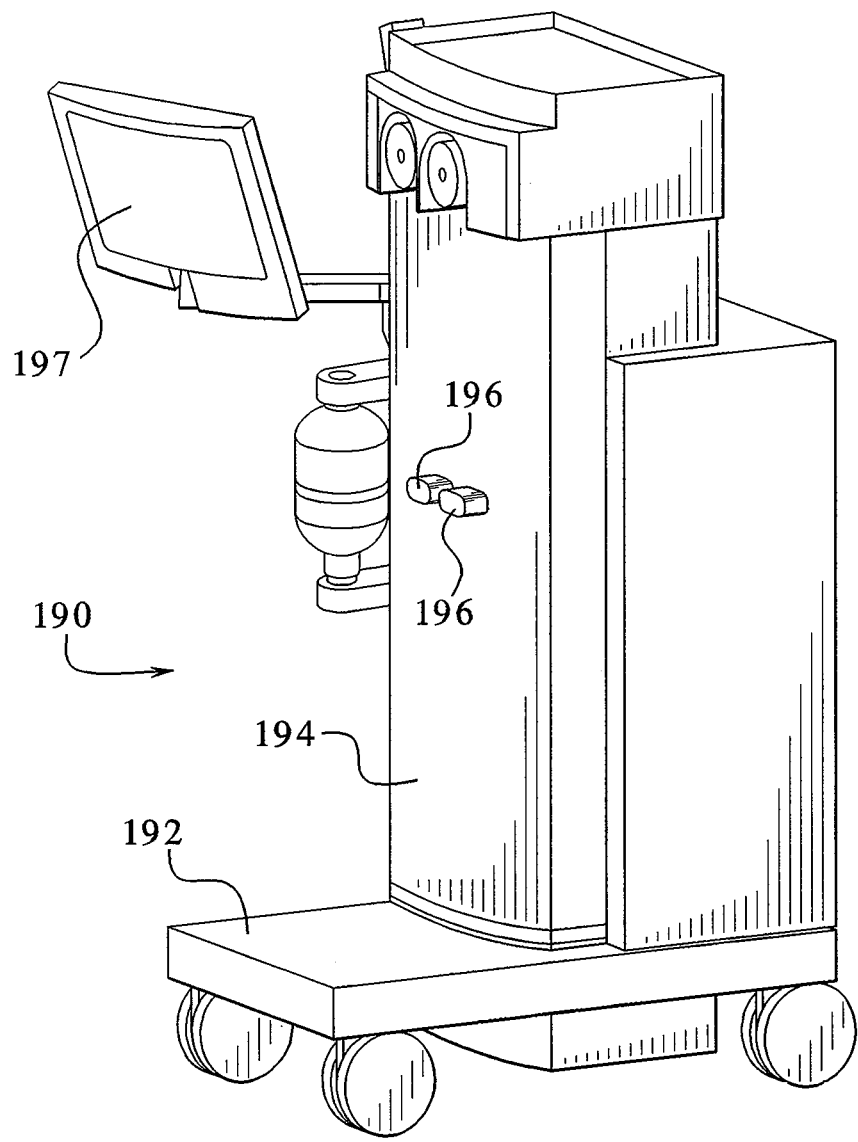
FIG. 4A schematically illustrates a hemodialysis machine in an embodiment of the present invention.
Figure 4B:
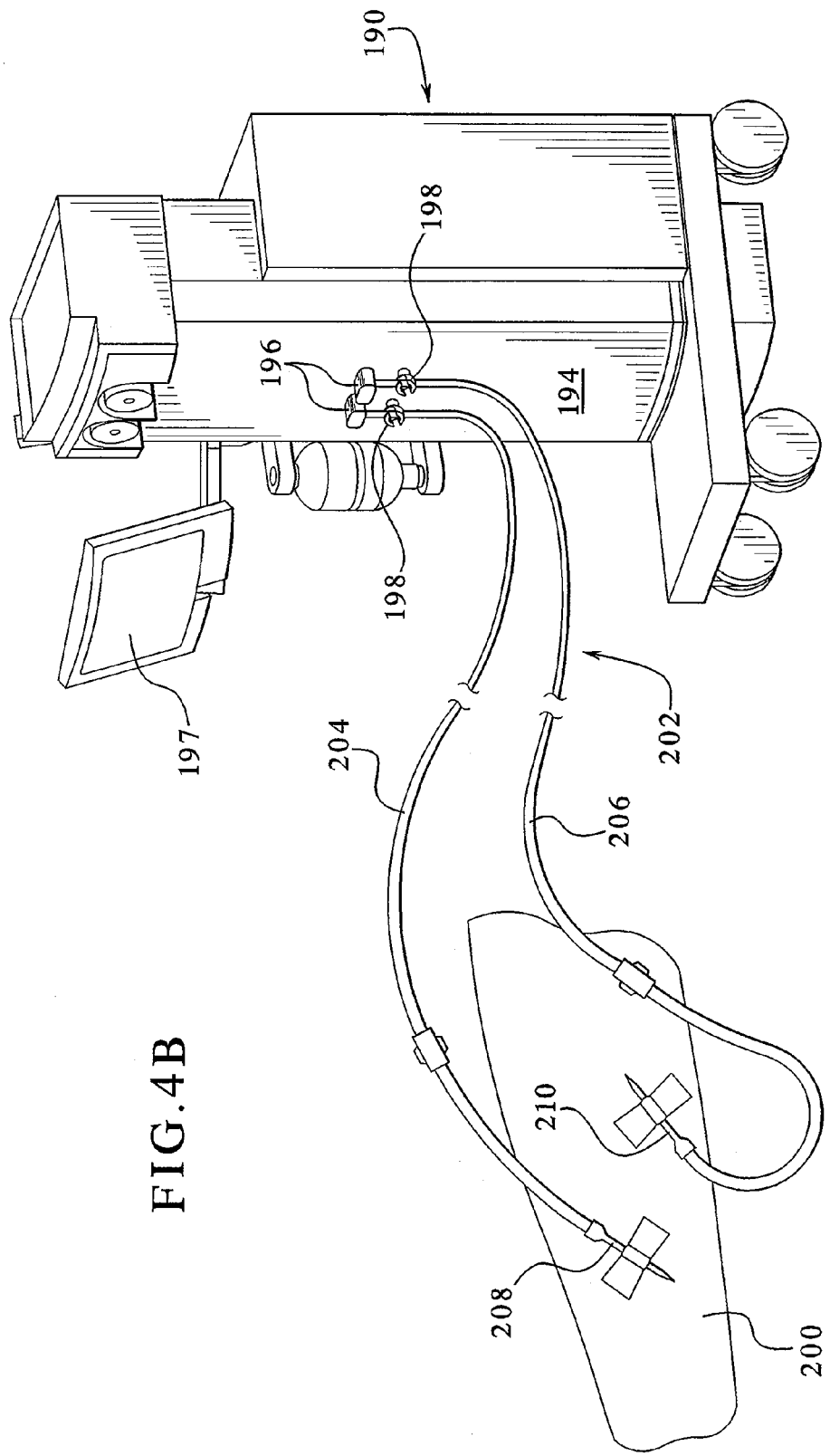
FIG. 4B schematically illustrates a hemodialysis machine coupled to a patient's access via a tubing set in an embodiment of the present invention.

The present invention can include any suitable dialysis machine for such purposes. An example, of a hemodialysis machine of the present invention is disclosed in U.S. Pat. No. 6,143,181 herein incorporated by reference. In an embodiment, the dialysis machine 190 includes a mobile chassis 192 and it has at the front side 194 thereof a common mechanism 196 for connecting tubing or the like by which a patient can be connected to the dialysis machine as shown in FIG. 4B. A flat touch screen 197 which can show several operational parameters and is provided with symbols and fields for adjustment of the dialysis machine by relevant symbols and fields, respectively, on the screen being touched can be adjusted vertically and can be universally pivoted on the dialysis machine and can be fixed in the desired adjusted position.

In an embodiment, the dialysis machine includes a chassis having one or more connectors for connecting a patient to the dialysis machine via a blood circuit allowing blood to flow between the patient and the dialysis machine during dialysis therapy wherein one or more electrical contacts are connected to the blood circuit in fluid communication with the blood allowing detection of a change in an electrical value in response to access disconnection as the blood flows through the blood circuit having an electrical signal passing therein.

In an embodiment, the dialysis machine of the present invention can be designed to accommodate one or more of the electrical contact coupling devices, such as a pair of coupling device, used to detect access disconnection as shown in FIG. 4B. For example, one or more coupling devices 198 can be attached to the front panel 194 of the dialysis machine 190. This can be done in any suitable way. In an embodiment, the a stem portion of the coupling device is insertably mounted via a threaded fit, frictional fit or the like, as previously discussed. This connects the patient to the dialysis machine 190 via a blood tubing set 202. The blood tubing set includes a first blood line 204 and a second blood line 206. In an embodiment, the first blood line 204 is connected to the patient via an arterial needle 208 or the like through which blood can flow from the patient 200 to the dialysis machine 190. The second blood line 206 is then connected to the patient 200 via a venous needle 210 or the like through which fluid flows from the dialysis machine to the patient thereby defining a blood circuit. Alternatively, the first blood line and the second blood line can be coupled to the venous needle and the arterial needle, respectively. The blood lines are made from any suitable medical grade material. In this regard, access disconnection, such as dislodgment of an arterial needle and/or a venous needle can be detected as previously discussed. Alternatively, the coupling device can be attached to the blood tubing set which is then attached to the dialysis machine in any suitable way.

Dialysis Treatment Centers

As previously discussed, the present invention can be used during dialysis therapy conducted at home and in dialysis treatment centers. The dialysis treatment centers can provide dialysis therapy to a number of patients. In this regard, the treatment centers include a number of dialysis machines to accommodate patient demands. The therapy sessions at dialysis treatment centers can be performed 24 hours a day, seven days a week depending on the locale and the patient demand for use.

In an embodiment, the dialysis treatment centers are provided with the capability to detect access disconnection during dialysis therapy pursuant to an embodiment of the present invention. For example, one or more of the dialysis machines can be adapted for use with an electrical contact coupling device along with the necessary other components to detect access disconnection as previously discussed.

In an embodiment, the electrical contact coupling device can be directly attached to one or more of the dialysis machines of the dialysis treatment center. It should be appreciated that the apparatuses, devices, methods and/or systems pursuant to an embodiment of the present invention can be applied for use during dialysis therapy administered to one or more patients in the dialysis treatment center in any suitable way. In an embodiment, the treatment center can have one or more patient stations at which dialysis therapy can be performed on one or more patients each coupled to a respective dialysis machine. Any suitable in-center therapy can be performed including, for example, hemodialysis, hemofiltration and hemodiafiltration and combinations thereof. As used herein, the term "patient station" or other like terms mean any suitably defined area of the dialysis treatment center dedicated for use during dialysis therapy. The patient station can include any number and type of suitable equipment necessary to administer dialysis therapy.

In an embodiment, the dialysis treatment center includes a number of patient stations each at which dialysis therapy can be administered to one or more patients; and one or more dialysis machines located at a respective patient station. One or more of the dialysis machines can include a chassis having one or more connectors for connecting a patient to the dialysis machine via a blood circuit allowing blood to flow between the patient and the dialysis machine during dialysis therapy wherein a pair of electrical contacts are connected to the blood circuit in fluid communication with the blood allowing detection of a change in an electrical value in response to access disconnection as the blood flows through the blood circuit having an electrical signal passing therein.

As previously discussed, the access disconnection detection capabilities of the present invention can be utilized to monitor and control a safe and effective dialysis therapy. Upon dislodgment of an access device, such as a needle, from the patient, the direct conductive measurement capabilities of the present invention can be used to provide a signal indicative of dislodgment that can be further processed for control and/or monitoring purposes. In an embodiment, the signal can be further processed to automatically terminate dialysis therapy to minimize blood loss due to dislodgment as previously discussed. Further, the signal can be processed to activate an alarm which can alert the patient and/or medical personnel to the dislodgment condition to ensure that responsive measures are taken. It should be appreciated that the present invention can be modified in a variety of suitable ways to facilitate the safe and effective administration of medical therapy, including dialysis therapy.

Applicants have found that the direct conductive measurement capabilities of the apparatus of the present invention can immediately detect blood loss or the like due to access disconnection, such as needle dislodgment, with high sensitivity and selectivity such that responsive measures can be taken to minimize blood loss due to same. The ability to act responsively and quickly to minimize blood loss upon detection thereof is particularly important with respect to needle dislodgment during hemodialysis. If not detected and responded to immediately, the amount of blood loss can be significant. In an embodiment, the present invention is capable of taking active or responsive measures, to minimize blood loss (i.e., shut-off blood pump, activate venous line clamp, activate alarm and/or the like) within about three seconds or less, preferably within about two to about three second upon immediate detection of needle dislodgment.

In addition, the controller can be utilized to monitor and/or control one or more treatment parameters during hemodialysis. These parameters can include, for example, the detection of blood due to blood loss upon needle dislodgment, the change in blood flow, the detection of air bubbles in the arterial line, detection of movement of the sensor during treatment, detection and/or monitoring of electrical continuity of the sensor or other like treatment parameters. In an embodiment, the controller includes a display (not shown) for monitoring one or more of the parameters. Thus, the present invention can be utilized to promote the safe and effective administration on patient therapy, such as dialysis therapy, as previously discussed.

As used herein "medical care provider" or other like terms including, for example, "medical care personnel", means an individual or individuals who are medically licensed, trained, experienced and/or otherwise qualified to practice and/or administer medical procedures including, for example, dialysis therapy, to a patient. Examples of a medical care provider include a doctor, a physician, a registered nurse or other like medical care personnel.

As used herein "non-medical care provider" or other like terms including, for example, "non-medical care personnel" means an individual or individuals who are not generally recognized as typical medical care providers, such as doctors, physicians, registered nurses or the like. Examples of non-medical care providers include patients, family members, friends or other like individuals.

As used herein "medical facility" or other like terms including, for example, "medical setting" means a facility or center where medical procedures or therapies, including dialysis therapies, are typically performed under the care of medical care personnel. Examples of medical facilities include hospitals, medical treatment facilities, such as dialysis treatment facilities, dialysis treatment centers, hemodialysis centers or the like.

As used herein "non-medical facility" or other like terms including, for example, "non-medical setting" means a facility, center, setting and/or environment that is not recognized as a typical medical facility, such as a hospital or the like. Examples of non-medical settings include a home, a residence or the like.

It should be appreciated that the electrode output signal can be combined with other less sensitive blood loss detection methods, such as venous pressure measurements, systemic blood pressure, the like or combinations thereof, to improve specificity to needle dislodgment.

Conductive Polymer

As previously discussed, the present invention provides conductive polymer materials and devices, apparatuses, systems and methods that employ same. The conductive polymer material can be utilized in a number of different applications, such as to monitor patient therapy. For example, the conductive polymer materials can be utilized to monitor patient access conditions as discussed above and as further detailed below. Other types of monitoring applications include, for example, monitoring solution mixing or compounding as described in greater detail below. The present invention contemplates monitoring one or a combination of condition changes associated with patient therapy, such as monitoring patient access conditions and solution mixing conditions, alone or in combination.

In an embodiment, the conductive polymer material includes a polymer matrix and a conductive component that is incorporated in the polymer matrix. Alternatively, the conductive polymer material, in an embodiment, includes a conductive polymer component without a separate conductive component, such as stainless steel. It should be appreciated that the conductive polymer material can be made from any suitable types and amounts of materials and in any suitable way.

As discussed above, the conductive polymer can include a polymer matrix and a conductive component incorporated in the matrix. The polymer matrix can include a variety of different polymer-based materials that are suitable for use in a variety of applications, particularly including medical applications, such as dialysis therapy. In an embodiment, the polymer matrix includes polyvinyl chloride, acrylonitrile butadiene styrene, polycarbonate, acrylic, a cyclo olefin copolymer, a cyclo olefin copolymer blend, a metallocene-based polyethylene, like polymeric materials and suitable combinations thereof.

The conductive component can include any suitable material or combination of materials that have conductive properties applicable for a number of different applications including, for example, detecting patient access disconnection during medical therapy as previously discussed, monitoring the mixing or compounding of solution components to form a mixed solution, and/or other like applications. Preferably, the conductive component includes stainless steel, fillers, carbon black, fibers thereof and/or the like.

The conductive component can be sized and shaped in any suitable way such that it can be readily incorporated in the polymer matrix. For example, the conductive component can include conductive fibers made from any suitable material, such as stainless steel, a carbonaceous material and/or the like. The fibers, in an embodiment, have an aspect ratio that ranges from about 2:1 to about 30:1.

The conductive polymer material can include any suitable amount of the conductive polymer matrix and the conductive component. This can vary depending on the application of the conductive polymer material. In an embodiment, the conductive component includes greater than about 10% by weight of the conductive polymer material. Preferably, the conductive component ranges from about 10% to about 50% by weight of the conductive polymer material. It should be appreciated that more than about 50% by weight of the conductive component can be utilized but may provide minimal, if any, increase in performance of the conductive polymer material depending on the application. Preferably, the conductive component is uniformly dispersed throughout the polymer matrix.

As previously discussed, the conductive polymer material, in an embodiment, is composed of a conductive polymer component. This type of component has sufficient electrical conductivity properties such that an additional conductive component, such as stainless steel, is not required. Examples of conductive polymer material components include polyaniline, polypyrrole, polythiophenes, polyethylenedioxythiophene, poly(p-phenylene vinylene), the like and mixtures thereof.

As previously discussed, the conductive polymer material can be made in any suitable way. In general, the conductive component is mixed with the polymer component under suitable processing conditions including temperature and pressure, for example, to form a polymer matrix with the conductive component incorporated therein. The mixing should take place over a suitable period of time and with a sufficient amount of force such that the conductive component is uniformly distributed throughout the polymer matrix.

The polymer matrix incorporated with a conductive component is then shaped and formed into a final product in any suitable way. For example, the polymer matrix incorporated with the conductive component can be formed into a single piece part via an injection molding process, extrusion process or the like under suitable processing conditions. Thus, the conductive polymer material can be readily made with manufacturing techniques, such as injection molding and extrusion. This can effectively provide a cost savings to the manufacturing process that can be inevitably passed along to the consumer.

The conductive polymer material can be formed into any suitable shape and size depending on the application. In an embodiment, the conductive polymer material is formed into an electrode or other like electrical contact that can be utilized for a number of different applications, including, for example, monitoring patient access conditions and/or monitoring solution mixing or compounding as discussed above and described below in greater detail. The conductive polymer electrode can have a variety of different and suitable configurations depending on the application. For example, the conductive polymer electrode can be made into a coupler that can be used to join tubing to form a tubing joint as described below.

As shown in FIGS. 5A and 5B, the conductive polymer coupler has a generally cylindrical shape. With this configuration, the conductive polymer can be readily attached to a tube through which fluid flows, thus forming a tubing joint.

As shown in FIG. 5A, the coupler 220 has a member 222 that extends from an inner surface 224 of the coupler electrode 220. The member 222 acts as a stop for the tube 226 that is attached to the electrode such that a desired length of the tubing joint 228 can be preset. The coupler 220 as shown in FIG. 5A, in an embodiment, is made via an injection molding process.

As shown in FIG. 5A, a first tube member 230 is attached to a first end 232 of the coupler 220 and positioned or stopped by a first end 234 of the member 222. A second tube member 236 is attached to a second end 238 of the coupler 220 and stopped or positioned by a second end 240 of the member 222. This forms a tubing joint 228, such as a tubing joint that is integrated within a blood circuit and utilized during dialysis therapy as described in the present application.

As shown in FIG. 5B, the coupler 242 is formed without a member that allows the length of the tubing joint to be preset as discussed above. In this regard, the tubing joint length can be adjusted accordingly depending on the application. Further, the coupler 242 as shown in FIG. 5B can be made via an extrusion process instead of an injection molding process. This can provide a further cost savings with respect to manufacturing of the coupler as compared to an injection molding process as discussed above. As shown in FIG. 5B, a first tube member 244 is attached to a first end 246 of the coupler 242 and a second tube member 248 is attached to the second end 250 of the coupler 242, thus forming the tubing joint 252.

The tube member can be attached to the conductive polymer coupler in any suitable way. For example, the conductive polymer material can be solvent bonded, heat sealed, laser welded, radio frequency sealed, or the like to the tubing.

The tubing can be made of any suitable material depending on the application. For example, the tubing can be made from polyvinyl chloride ("PVC"). Preferably, the PVC tubing is attached to a conductive polymer material that is made with a polymer matrix composed of acrylonitrile butadiene styrene ("ABS") where the ABS-based conductive material is solvent bonded to the PVC tubing.

However, the tubing can be made of a variety of different materials depending on the application. In an embodiment, the tubing includes a non-PVC material, such as metallocene-based polyethylene polymers, cyclo olefin copolymers, cyclo olefin copolymer blends and the like. The non-PVC materials can include any suitable type and amount of constituents. Metallocene-based polyethylene polymers and the like illustrative of the present invention can be found, for example, in U.S. Pat. No. 6,372,848, the disclosure of which is herein incorporated by reference. These types of non-PVC polymers can include a polymer blend that has a first ethylene and α-olefin copolymer obtained using a single site catalyst present in an amount by weight of from about 0% to about 99% by weight of the blend and having a melt flow index from fractional, such as about 0.1 g/10 min to about 5 g/10 min, a second ethylene and α-olefin copolymer obtained using a single site catalyst and being present in an amount by weight of the blend from about 0% to about 99% and having a melt flow index from higher than about 5 g/10 min to about 20 g/10 min; and a third ethylene and α-olefin copolymer obtained using a single-site catalyst and being present in an amount by weight of the blend from about 0% to about 99% and having a melt flow index greater than about 20 g/10 min. In an embodiment, the α-olefin copolymer has a molecular weight distribution of less than about 3.

Cyclo olefin copolymers and blends thereof illustrative of the present invention can be found, for example, in U.S. Pat. No. 6,255,396, the disclosure of which is herein incorporated by reference. These types of non-PVC polymers can include as a component homopolymers or copolymers of cyclic olefins or bridged polycyclic hydrocarbons. For example, the polymer composition includes a first component obtained by copolymerizing a norbomene monomer and an ethylene monomer wherein the first component is in an amount from about 1-99% weight of the composition; and a second component of an ethylene and α-olefin copolymer that has six carbons wherein the second component is in an amount from about 99% to about 1% by weight of the composition. In an embodiment, the polymer composition can include an additional component, such as a second homopolymer or copolymer of a cyclic olefin or a bridged polycyclic hydrocarbon.

The non-PVC based tubing and the non-PVC based conductive coupler can be joined in any suitable way to form a tubing joint. In an embodiment, the non-PVC based tubing and coupler are joined via solvent bonding, such as disclosed in U.S. Pat. Nos. 6,255,396 and 6,372,848. As used herein the term solvent bonding or other like terms means that the tubing can be exposed to a solvent to melt, dissolve or swell the tubing and then be attached to another polymeric component to form a permanent bond. Suitable solvents typically include those having a solubility parameter of less than about 20 $(Mpa)^{1/2}$. Suitable solvents can also have a molecular weight less than about 200 g/mole. The solvent can include, for example, aliphatic hydrocarbons, aromatic hydrocarbons, and mixtures thereof. As used herein, the terms aliphatic hydrocarbon and aromatic hydrocarbon are compounds containing only carbon and hydrogen atoms.

Suitable aliphatic hydrocarbons can include substituted and unsubstituted hexane, heptane, cyclohexane, cycloheptane, decalin and the like. Suitable aromatic hydrocarbons can include substituted and unsubstituted aromatic hydrocarbon solvents, such as xylene, tetralin, toluene, cumene and the like. Suitable hydrocarbon substituents can include aliphatic substituents that have from 1-12 carbons and include propyl, ethyl, butyl, hexyl, tertiary butyl, isobutyl, the like and combinations thereof.

Figure 6:
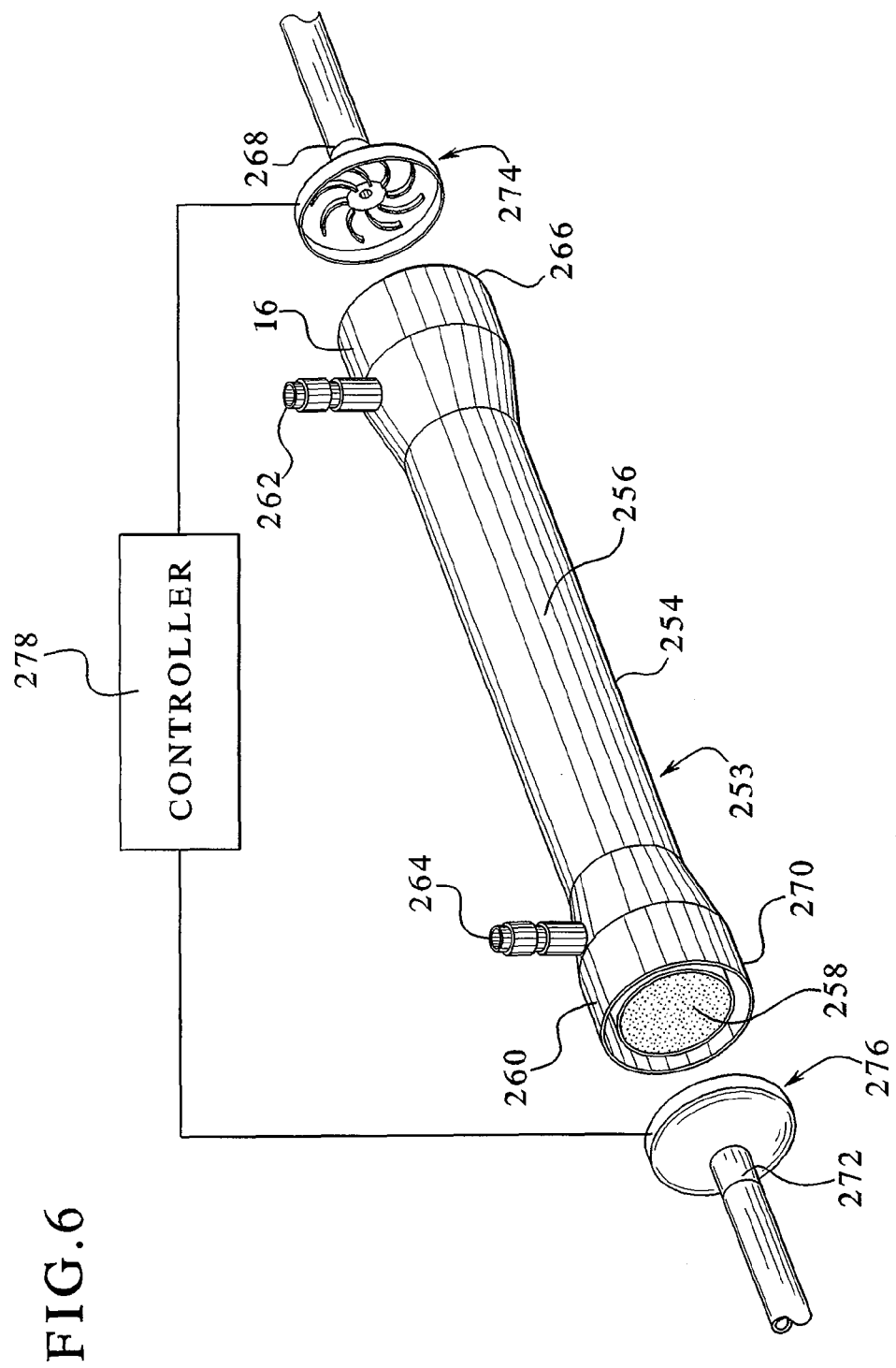
FIG. 6 illustrates a dialyzer according to an embodiment of the present invention.

As previously discussed, the conductive polymer of the present invention can be constructed and arranged into a variety of different configurations, such as a conductive polymer coupler as shown in FIGS. 5A and 5B and discussed above. Another example includes a dialyzer header that is made from the conductive polymer according to an embodiment. Referring to FIG. 6, a dialyzer 253 is generally illustrated. The dialyzer 253 includes a body member 254 that generally includes a casing 256. The casing 256 includes a core section as well as two bell members 260 located at each end of the dialyzer. Located within the core is a fiber bundle 258. The dialyzer also includes a dialysate inlet 262 and a dialysate outlet 264.

Located at a first end 266 of the dialyzer 253 is a fluid inlet 268 and at a second end 270 is a fluid outlet 272 defined by a fluid inlet header 274 and a fluid outlet header 276, respectively. The dialyzer 253 is connected to a dialysis blood circuit in any suitable manner. In an embodiment, the inlet 274 and outlet 276 headers are made from the conductive polymer material of the present invention as discussed above. The inlet 274 and outlet 276 headers can be connected to a controller 278 such that the conductive polymer headers can be utilized to monitor patient access conditions as previously discussed.

A variety of different header and dialyzer designs can be utilized. For example, U.S. Pat. No. 6,623,638 and U.S. Patent Publication No. 2003/0075498 provide a number of different examples illustrative of the present invention. The disclosures of U.S. Pat. No. 6,623,638 and U.S. Patent Publication No. 2003/0075498 are herein incorporated by reference.

The conductive polymer of the present invention can be utilized in any suitable way and in a variety of different devices, apparatuses, systems and applications thereof. For example, the conductive polymer can be utilized to detect a change in impedance in response to dislodgement of an access device, to detect a change in conductivity in response to a change in solution composition and/or other suitable applications.

In an embodiment, the conductive polymer is part of a sensor assembly or apparatus that can be utilized, for example, for monitoring dialysis applications as discussed in the present application. The sensor apparatus of the present invention can include a number of different configurations and designs. Two examples of such designs illustrative of the present invention are described below in FIGS. 7A and 7B.

In FIG. 7A, the tubing joint 284 that includes the conductive polymer electrode 286 attached to a tube member 288 as described above, for example, is positioned in place by a holding device 290 or holder for purposes of detection capabilities associated with the sensor apparatus 291 in an embodiment. In general, the holder 290 as shown in FIG. 7A has a hub design. More specifically, the holder 290 includes a base member 292 onto which the tubing joint 284 can be placed. The base member 292 includes a first portion 294 that is made from a plastic or other suitable material. The first portion 294 defines an outer surface 296 of the base member 292. Along the outer surface 296, the first portion 294 includes two openings that are spaced apart as shown in FIG. 7A. The first opening 298 is located on a first edge 300 of the first portion of the base and the second opening 302 is located on a second edge 304 of the first portion of the base. The openings can be configured in any suitable way and be utilized for mounting purposes.

The second portion of the base member includes a conductive portion 306 as shown in FIG. 7A. In an embodiment, the conductive portion 306 includes a single piece part 308 that is made from any suitable conductive material, such as stainless steel and/or the like. As shown in FIG. 7A, the conductive polymer of the tubing joint is placed against a curved edge 310 of the second portion that substantially forms to an outer surface 312 of the conductive polymer electrode 286. The electrode is substantially cylindrical in shape.

The holder 290 further includes an arm member 314 that is pivotally attached to the base member 292 as shown in FIG. 7A. The arm member 314 includes a generally curved region such that the arm 314 can be positioned over the tubing joint 284 allowing it to substantially conform to the generally cylindrical surface of the tube joint and thus further securing the tubing joint 284 in place.

Another configuration of a hub design illustrative of the sensor apparatus of the present invention is shown in FIG. 7B. In general, this design provides a box-like holder 316 that encloses the tubing joint 318 wherein the tubing joint includes the conductive polymer electrode 320 in the form of a coupler that is attached to the tube member 322 as discussed above. The holder 316 includes a base member 324. The base member 324 includes side portions 326, a bottom portion 328 and an opening 330 at a top portion 332. As shown in FIG. 7B, the sensor apparatus 334 includes a conductive member 336 that is contained in the base member 324. The conductive member 336 can be made of any suitable material as described above. The conductive member 336 includes an annular-shaped surface 338 against which the tubing joint 318 can be placed. The sensor apparatus 334 further includes a lid 340 that is pivotally attached to the base member 324. The lid 340 has a member 342 that abuts against a portion of the tubing joint in a closed position. This secures the tubing joint in place for use.

As previously discussed, the sensor apparatus of the present application can be used in a number of suitable applications. For example, the sensor apparatus can be suitably coupled to a blood circuit and used for purposes of detecting disconnection of an access device as described in the present application. Another application includes the monitoring of solution compounding as described in greater detail below. In this regard, the sensor apparatus as shown in FIGS. 7A and 7B can be used in combination with or in place of the electrical coupling devices as illustrated in FIGS. 2A-2E and further described above. Thus, the present invention can be utilized to monitor one or a combination of conditions, such as patient access and solution mixing, during use. As applied, the sensor apparatus can be connected to a controller or other like device for detection purposes. The controller can include one or a number of different devices that are in electrical contact with the sensor apparatus in any suitable way.

In another embodiment, the sensor apparatus can include a single piece part that is made from the conductive polymer material. The single piece part can be made in any suitable way such as through injection molding as described above. A number of different and suitable shapes and sizes can be formed. One such example illustrative of the present invention of a single piece part conductive electrode 344 is shown in FIGS. 8A and 8B.

Figure 8A:
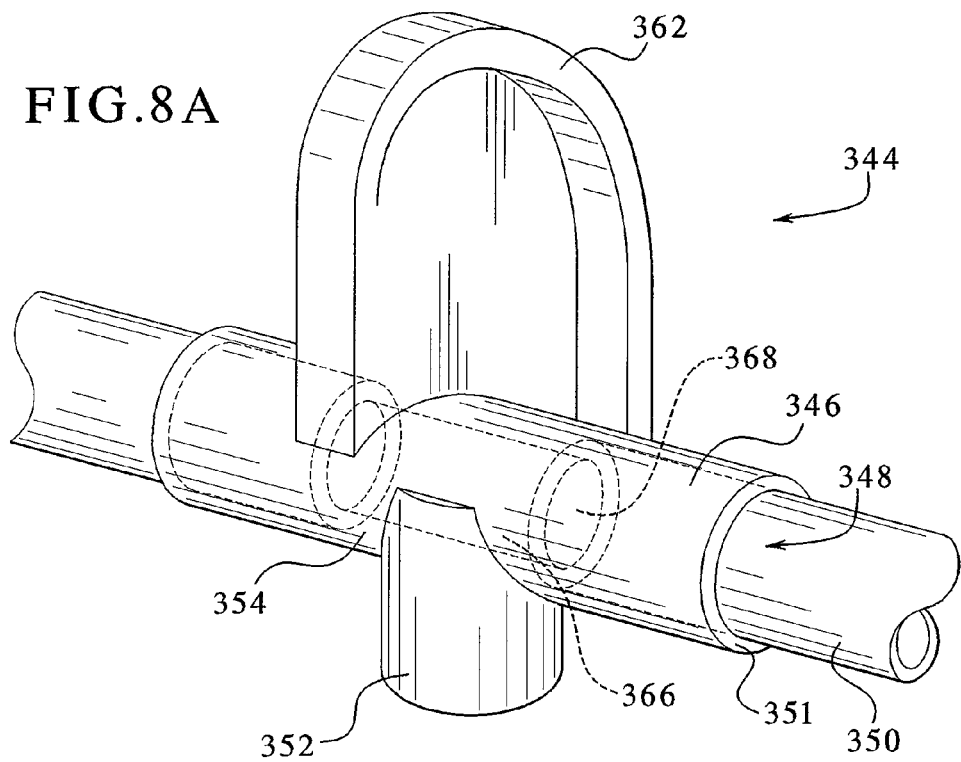
FIGS. 8A and 8B illustrate a single-piece sensor according to an embodiment of the present invention.
Figure 8B:
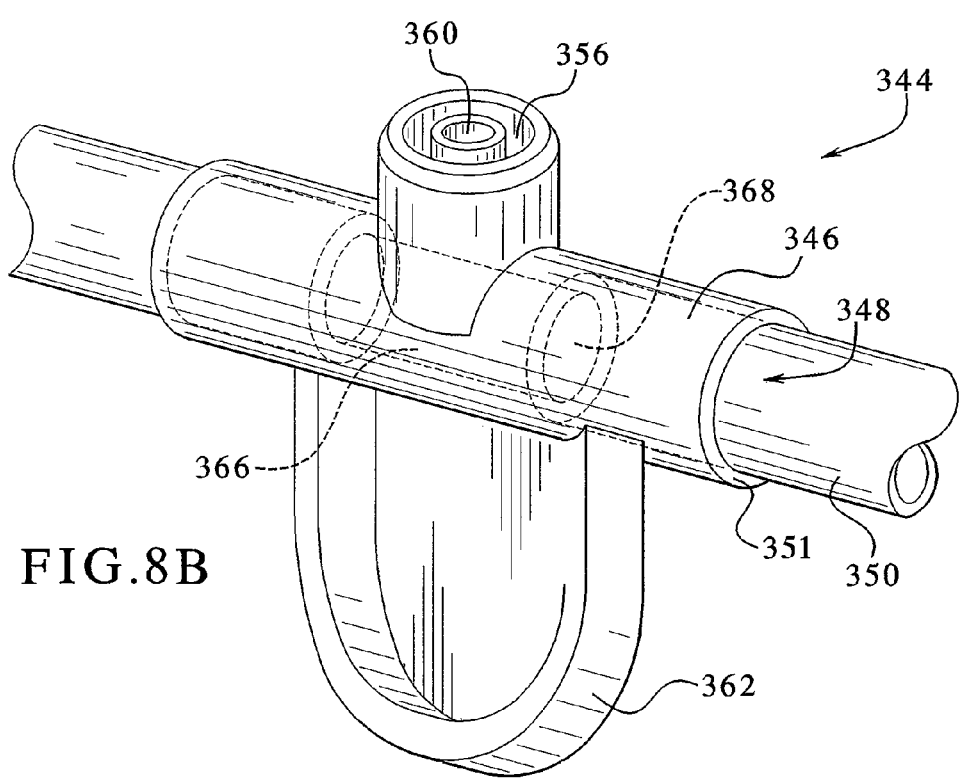

In general, the conductive polymer electrode 344 is configured as a coupler that can join tubing to form a tubing joint through which fluid can flow as shown in FIGS. 8A and 8B. The conductive polymer electrode 344 includes a base member 346 that has an annular opening 348 extending therethrough. A tube member 350 can be attached to the ends 351 of the annular opening 348 such that the tubing joint can be formed as described above. The base member 346 includes a stem portion 352 that extends from a portion of a surface 354 of the base member 346. This can be used to mount or attach the conductive polymer electrode 344 to a control panel or other suitable component, such as a hemodialysis machine as described above. The stem portion 352 defines an annular-shaped channel 356 that ends from the surface 354 of the base member 346. Within the annular-shaped channels, an inner annular-shaped channel 360 is also provided that extends from the surface 354 of the base 346, as shown in FIG. 8B. The stem portion can be utilized to provide a pathway through which the electrode can be in electrical contact with one or more other devices, such as a controller, in any suitable way.

The base member further includes a top member 362 that extends from a portion of the surface 354 of the base member 346. The top member 362 can be used to secure the stem portion 352 of the base member 346 in place for use and/or to remove the electrode after use.

As shown in FIGS. 8A and 8B, the conductive polymer electrode 344 includes a member 366 that extends from an inner surface of the annular opening 348. The member 366 acts as a stop against which the tubing can be placed to form the tubing joint. The member 366 has a generally-cylindrical shape with an opening 368 through which fluid can flow.

As previously discussed, the conductive polymer material of the present invention can be utilized in a number of different applications. In an embodiment, the conductive polymer material can be utilized to monitor patient access conditions, such as to detect disconnection of an access device that is inserted in a patient through which fluid flows during medical therapy. Preferably, the disconnection detection application is applied during dialysis therapy, such as during hemodialysis therapy.

As applied to dialysis applications, the conductive polymer can be formed into an electrode and attached to a dialysis blood circuit in any suitable manner. As shown in FIGS. 1A and 2A and further described above, at least one of the sensors can include an electrode made with the conductive polymer material of the present invention. The sensors 22 and 24 are in electrical contact with a controller 29 and thus the conductive polymer electrode can be utilized for detection, monitoring and control purposes related to dialysis therapy as described above. As shown in FIGS. 4A and 4B and described in the present application, the sensors 198 can be attached directly to the hemodialysis machine wherein at least one of the sensors includes a conductive polymer electrode according to an embodiment of the present invention. The conductive polymer sensor can be configured in any suitable way, such as the coupler and hub design (See, FIGS. 5A, 5B, 7A and 7B), the single-piece part design (See, FIGS. 8A and 8B) and dialyzer header design (See, FIGS. 8A and 8B) as described above. It should be appreciated that the present invention contemplates the use of one or a combination of different sensors to monitor medical therapy, such as patient access and solution mixing conditions.

In an embodiment, the conductive polymer material of the present invention can be utilized for monitoring the mixing of solutions to form a mixed solution, such as a mixed solution used during medical therapy. One type of application illustrative of the present invention for such monitoring purposes is during dialysis therapy, particularly during peritoneal dialysis. In general, the conductive polymer material can be formed into an electrode or other sensing device that can effectively detect changes in conductivity associated with a dialysis solution that is administered to the patient during peritoneal dialysis.

The dialysis solution can be formed from a number of solution components that are mixed to form a mixed dialysis solution prior to administration. The dialysis solution components can have varying pH levels, such as ranging from about 1.8 to about 9.2. Once mixed, the pH of the mixed dialysis solution should be at a physiologically acceptable level, such as ranging from about 6.8 to about 7.5, prior to use. The pH level can be monitored in relation to changes in the conductivity level of the dialysis solution. In this regard, the conductive polymer of the present invention can be utilized to detect changes in conductivity level and thus can be utilized to determine whether the solution components are properly mixed to form the mixed dialysis solution at an acceptable pH level prior to use. A general description of peritoneal dialysis is provided below and is illustrative of the present invention.

Peritoneal dialysis utilizes a sterile dialysis solution, which is infused into a patient's peritoneal cavity and into contact with the patient's peritoneal membrane. Waste, toxins and excess water pass from the patient's bloodstream through the peritoneal membrane and into the dialysis solution. The transfer of waste, toxins, and excess water from the bloodstream into the dialysis solution occurs due to diffusion and osmosis during a dwell period as an osmotic agent in the dialysis solution creates an osmotic gradient across the membrane. The spent solution is later drained from the patient's peritoneal cavity to remove the waste, toxins and excess water from the patient.

There are various types of peritoneal dialysis therapies, including continuous ambulatory peritoneal dialysis ("CAPD") and automated peritoneal dialysis. CAPD is a manual dialysis treatment, in which the patient connects the catheter to a bag of fresh dialysis solution and manually infuses fresh dialysis solution through the catheter or other suitable access device and into the patient's peritoneal cavity. The patient disconnects the catheter from the fresh dialysis solution bag and allows the solution to dwell within the cavity to transfer waste, toxins and excess water from the patient's bloodstream to the dialysis solution. After a dwell period, the patient drains the spent dialysis solution and then repeats the manual dialysis procedure. Tubing sets with "Y" connectors for the solution and drain bags are available that can reduce the number of connections the patient must make. The tubing sets can include pre-attached bags including, for example, an empty bag and a bag filled with dialysis solution.

In CAPD, the patient performs several drain, fill, and dwell cycles during the day, for example, about four times per day. Each treatment cycle, which includes a drain, fill and dwell, takes about four hours.

Automated peritoneal dialysis is similar to continuous ambulatory peritoneal dialysis in that the dialysis treatment includes a drain, fill, and dwell cycle. However, a dialysis machine automatically performs three or more cycles of peritoneal dialysis treatment, typically overnight while the patient sleeps.

With automated peritoneal dialysis, an automated dialysis machine fluidly connects to an implanted catheter. The automated dialysis machine also fluidly connects to a source or bag of fresh dialysis solution and to a fluid drain. The dialysis machine pumps spent dialysis solution from the peritoneal cavity, through the catheter, to the drain. The dialysis machine then pumps fresh dialysis solution from the source, through the catheter, and into the patient's peritoneal cavity. The automated machine allows the dialysis solution to dwell within the cavity so that the transfer of waste, toxins and excess water from the patient's bloodstream to the dialysis solution can take place. A computer controls the automated dialysis machine so that the dialysis treatment occurs automatically when the patient is connected to the dialysis machine, for example, when the patient sleeps. That is, the dialysis system automatically and sequentially pumps fluid into the peritoneal cavity, allows for dwell, pumps fluid out of the peritoneal cavity, and repeats the procedure.

Several drain, fill, and dwell cycles will occur during the treatment. Also, a final volume "last fill" is typically used at the end of the automated dialysis treatment, which remains in the peritoneal cavity of the patient when the patient disconnects from the dialysis machine for the day. Automated peritoneal dialysis frees the patient from having to manually perform the drain, dwell, and fill steps during the day.

In general, the dialysis solution includes an osmotic agent, such as dextrose or other suitable constituent in any suitable amount, such as from about 1.5% to about 4.25% by weight. The dialysis solution further includes one or more electrolytes, such as sodium, calcium, potassium, magnesium chloride and/or the like in any suitable amount. The dialysis solution may also include other constituents, such as buffers including lactate and bicarbonate, or the like, and other constituents, such as stabilizers. The dialysis solution can be made from multiple solution components that can vary in the amounts and types of constituents thereof and have varying pH levels.

A variety of different and suitable types of multi-part dialysis solutions can be utilized. For example, a multi-part bicarbonate-based solution can be found in U.S. patent application Ser. No. 09/955,248, now U.S. Pat. No. 7,011,855, issued Mar. 14, 2006, entitled BIOCHEMICALLY BALANCED PERITONEAL DIALYSIS SOLUTIONS, filed on Sep. 17, 2001, the disclosure of which is incorporated herein by reference. An example of a multi-part lactate-based solution can be found in U.S. patent application Ser. No. 10/628,065, now U.S. Pat. No. 7,053,059, issued May 30, 2006, entitled DIALYSIS SOLUTIONS WITH REDUCED LEVELS OF GLUCOSE DEGRADATION PRODUCTS, filed on Jul. 25, 2003 the disclosure of which is herein incorporated by reference.

Another example of a bicarbonate-based solution can be found in U.S. patent application Ser. No. 10/044,234, now U.S. Pat. No. 7,122,210, issued Oct. 17, 2006, entitled BICARBONATE-BASED SOLUTIONS FOR DIALYSIS THERAPIES, filed on Jan. 11, 2002 and as further disclosed in U.S. Pat. No. 6,309,673, the disclosures of which are herein incorporated by reference. The bicarbonate-based solution can be made from solution components that have varying pH conditions, such as under moderate and extreme pH conditions. In an embodiment, the solution components can vary in pH from between about 1.0 to about 10.0. Once mixed, the desired pH of the mixed solution is a physiological acceptable level, such as between about 6.5 to about 7.6 (i.e., close to the pH of blood).

For example, under moderate pH conditions, the bicarbonate-based solution can be formulated by the mixing of a bicarbonate concentrate with a pH that ranges from about 7.2 to about 7.9, preferably from about 7.4 to about 7.6, and an electrolyte concentrate with a pH that ranges from about 3.0 to about 5.0. Under extreme pH conditions, for example, the bicarbonate concentrate has a pH that can range from about 8.6 to about 9.5 and is mixed with an electrolyte concentrate that has a pH from about 1.7 to about 2.2. A variety of different and suitable acidic and/or basic agents can be utilized to adjust the pH of the bicarbonate and/or electrolyte concentrates. For example, a variety of inorganic acids and bases can be utilized, such as hydrochloric acid, sulfuric acid, nitric acid, hydrogen bromide, hydrogen iodide, sodium hydroxide, the like or combinations thereof.

The solution components, such as the electrolyte concentrate and the dextrose concentrate, can then be mixed in the solution bag and then administered as a mixed solution to the patient during peritoneal dialysis. An illustrated example of a multi-chamber container that separately contains solution components of a dialysis solution according to embodiment of the present invention is shown in FIG. 9.

It should be appreciated that the components of the dialysis solutions of the present invention can be housed or contained in any suitable manner such that the dialysis solutions can be effectively prepared and administered. In an embodiment, the present invention includes a multi-part dialysis solution in which two or more parts are formulated and stored separately, and then mixed just prior to use. A variety of containers can be used to house the various parts of the dialysis solution, such as separate containers (i.e., flasks or bags) that are connected by a suitable fluid communication mechanism.

In an embodiment, a multi-chamber container or bag can be used to house the separate components of the solution including, for example, a dextrose concentrate and a buffer concentrate. In an embodiment, the separate components are mixed within the multi-chamber bag prior to use, such as applied during peritoneal dialysis.

Figure 9:
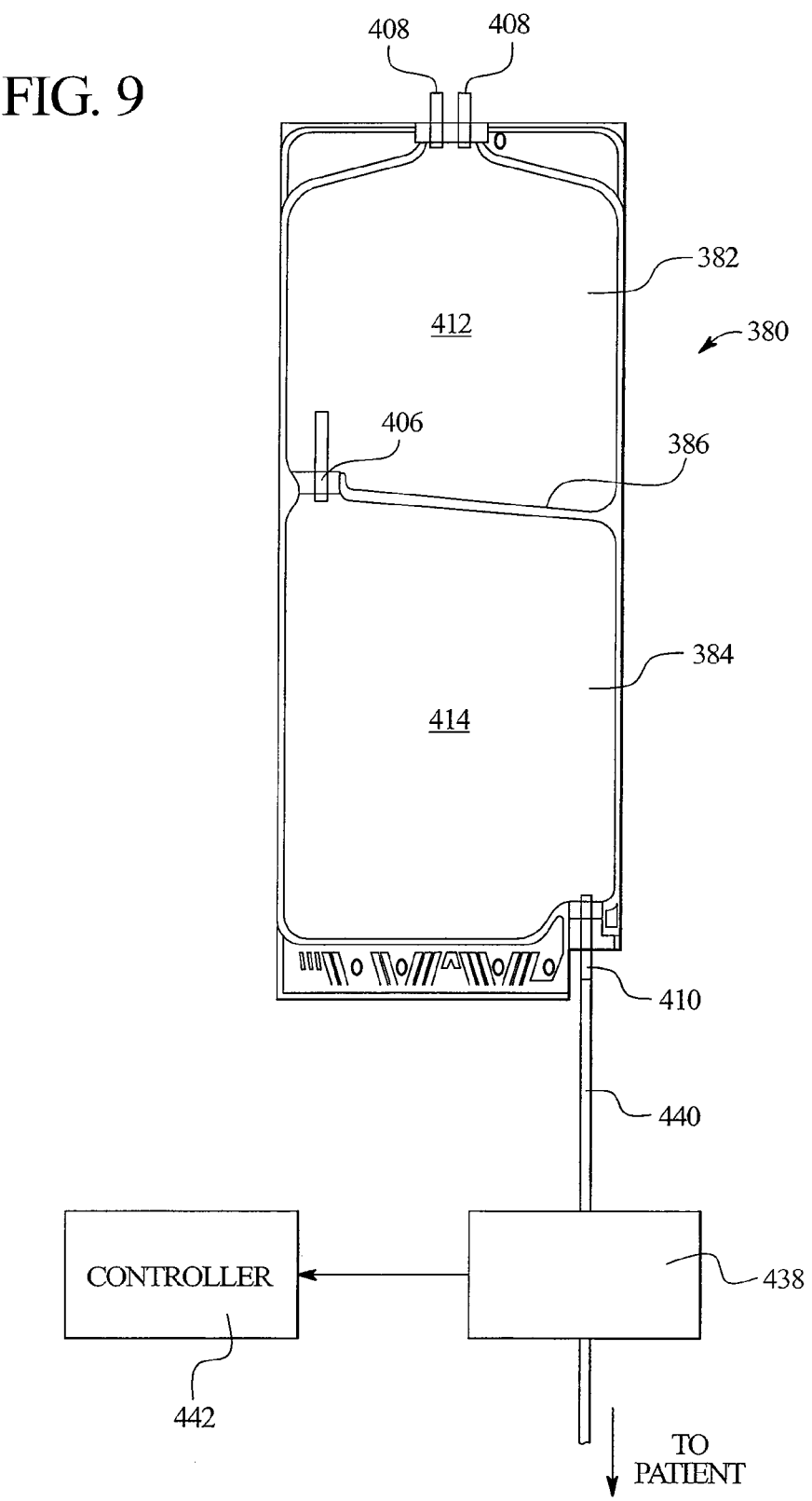
FIG. 9 illustrates a multi-chamber bag according to an embodiment of the present invention.

FIG. 9 illustrates a suitable container for storing, formulating, mixing and administering a dialysis solution, such as during continuous ambulatory peritoneal dialysis, according to an embodiment of the present invention. The multi-chamber bag 380 has a first chamber 382 and a second chamber 384. The interior of the container is divided by a heat seal 386 into the two chambers. It should be appreciated that the container can be divided into separate chambers by any suitable seal.

Figure 10:
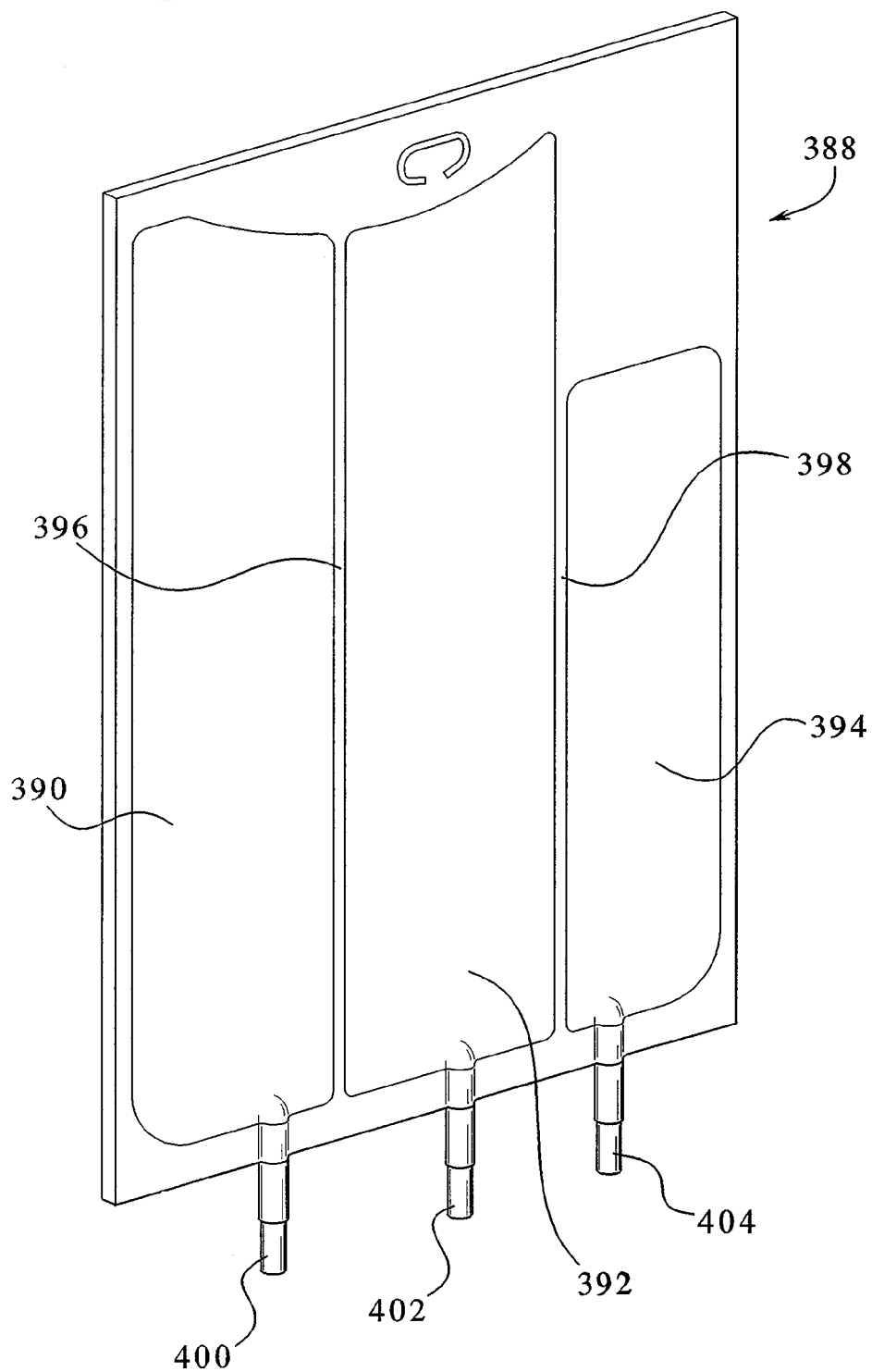
FIG. 10 illustrates a multi-chamber bag with a peelable seal according to an embodiment of the present invention.

In an embodiment, the container can be divided into separate chambers, such as two or more chambers, by a peel seal. With the use of a peel seal, a frangible connector or other suitable type of connector would not be required to mix the solution components within the multi-chamber bag. An example of a multi-chamber solution bag that includes a peel seal is disclosed in U.S. Pat. No. 6,319,243, the disclosure of which is herein incorporated by reference. As shown in FIG. 10, a container 388 includes at least three chambers 390, 392 and 394. The chambers 390, 392 and 394 are designed for the separate storage of liquids and/or solutions, that can be mixed within the container to form a mixed solution ready-for-use. It should be appreciated that more or less than three chambers can be utilized.

The peelable seals 396 and 398 are provided between the chambers 390, 392 and 394, respectively. Examples of peelable seals can be found in U.S. patent application Ser. No. 08/033,233 filed on Mar. 16, 1993, now abandoned, entitled "PEELABLE SEAL AND CONTAINER HAVING SAME", the disclosure of which is herein incorporated by reference. The peelable seals allow for the selective opening of the chambers to allow for the selective mixing of the liquids contained therein.

The container 388 can also include tubular ports, such as tubular ports 400, 402 and 404 as shown in FIG. 10. The tubular ports are mounted to the container so as to allow fluid communication with the container and specifically with chambers 390, 392 and 394. To this end, the tubular ports 400, 402 and 404 can include a membrane that is pierced, for example, by a cannula or a spike or an administration set for delivery of the contents of the container to the patient. It should be appreciated that more or less than three ports can be utilized.

As shown in FIG. 9, the multi-chamber container 380 has a frangible connector 406 to sealingly couple the first chamber 382 to the second chamber 384 instead of a peelable seal. To mix the solution within the multi-chamber bag 380, the frangible connector 406 is broken.

The first container or chamber 382 includes two port tubes 408 of suitable sizes and lengths. It should be appreciated that more or less than two port tubes may be used. One of the port tubes, for example, can be utilized to add other constituents to the first chamber 382 during formulation of the solution of the present invention, if necessary. The remaining port tube, for example, can be utilized to adaptedly couple the first chamber 382 to the patient via a patient's administration line (not shown), be used to add additional other constituents or the like. The second container or chamber 384 has a single port tube 410 extending there from. In an embodiment, the port tube 410 is connected to a patient's administration line through which a solution can flow to the patient once the solution is mixed as described below.

In an embodiment, the transfer of product within the multi-chamber bag 380 can be initiated from the first chamber 382 to the second chamber 384 such that the components of each chamber can be properly mixed to form the dialysis solution of the present invention. In an embodiment, a dextrose concentrate 412 is contained in the first chamber 382 and a buffer concentrate 414 is contained in the second chamber 384. It should be appreciated that any suitable type or number of solution components can be separated with a multi-chamber bag and then mixed to form a mixed solution prior to administration to the patient. Illustrative examples of peritoneal dialysis solutions include those described in U.S. patent application Ser. Nos. 09/955,298, now abandoned, and 10/628,065, now U.S. Pat. No. 7,053,059, issued May 30, 2006, and U.S. Pat. No. 6,309,673 as described above.

The first chamber 382 is smaller in volume than the second chamber 384 such that the components of each chamber can be properly mixed once the transfer from the first chamber to the second chamber has occurred. Thus, the multi-chamber bag 380 can house at least two solution component parts that after mixture will result in a ready-to-use dialysis solution. An example of the multi-chamber container is set forth in U.S. Pat. No. 5,431,496, the disclosure of which is incorporated herein by reference. The multi-chamber bag can be made from a gas permeable material, such as polypropylene, polyvinyl chloride or the like.

It should be appreciated that the multi-chamber bag can be manufactured from a variety of different and suitable materials and configured in a number of suitable ways such that the dialysis solutions of the present invention can be effectively formulated and administered to the patient during medical therapy in any suitable manner. For example, the first chamber can be larger in volume than the second chamber and further adapted such that the dialysis solution of the present invention can be readily and effectively made and administered to the patient.

In an embodiment, the dialysis solution is contained and administered from a multi-chamber solution bag during peritoneal dialysis, such as during CAPD. The solution bag can include multiple chambers that each contain separate components of the dialysis solution prior to mixing as discussed above. This may be necessary to maintain separation of the non-compatible solution components prior to mixing for purposes of stability, sterility, effectiveness or the like associated with the dialysis solution prior to use.

Figure 11:
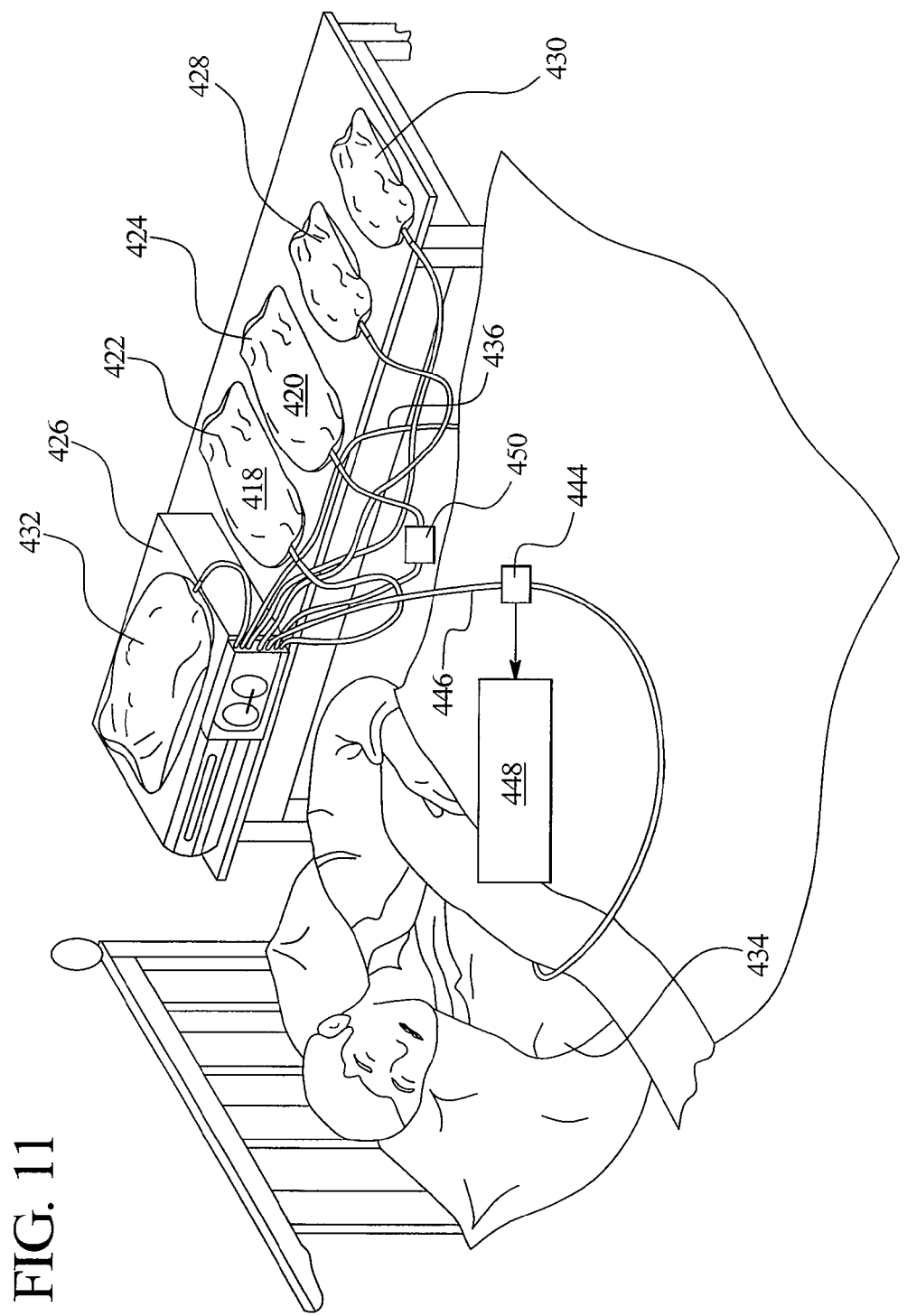
FIG. 11 illustrates an automated peritoneal dialysis system according to an embodiment of the present invention.

In another embodiment, the solution components can be prepared and stored in separate containers and then mixed via an admix device prior to use, such as applied during automated peritoneal dialysis. As shown in FIG. 11, a first solution component, such as a dextrose concentrate 416 and a second solution component, such as a buffer concentrate 420 are stored in the respective separate containers 422 and 424 or bags which are fluidly connected to an admix device 426 suitable for use during automated peritoneal dialysis, an example of which includes ADMIX HOMECHOICE by BAXTER INTERNATIONAL, INC. In addition to the first and second components, a first bag 428 and last bag 430 filled with a suitable solution can also be used during dialysis therapy as generally known.

In an embodiment, an effective amount of the first solution component 416 and the second solution component 420 are drawn from each respective container and into a heater bag 432 where the solution components (e.g., dextrose and buffer concentrates) can be mixed and heated prior to infusion into a patient 434 during dialysis therapy. As further shown in FIG. 11, a drain line 436 is coupled to the admix device 426 from which waste fluids can be removed from the patient during therapy.

According to an embodiment of the present invention, the conductive polymer material can be used as a sensor to monitor solution compounding, such as during peritoneal dialysis. For example, the conductive polymer sensor 438 can be attached to a tube 440 through which the mixed dialysis solution flows to the patient from the multi-chamber solution bag 380 as shown in FIG. 9. The conductive polymer sensor 438 is in electric contact with a controller 442 or other like device such that a change in conductivity of the mixed dialysis solution that is fed to the patient can be monitored. Based on the conductivity level, one can monitor the pH level of the mixed solution to determine whether the solution components (e.g., dextrose concentrate and buffer concentrate) have been properly and sufficiently mixed to form the dialysis solution prior to use. If the dialysis solution is not properly mixed, the conductivity level will exist above or below a baseline conductivity level that is generally associated with a desired pH level of a dialysis solution that is ready-for-use. As previously discussed, the desired pH of the mixed dialysis solution is maintained at a physiological acceptable level, such as between about 6.5 to about 7.6 prior to use. Based on this information, adjustments can be made to the process such that the solution chemistry of the dialysis solution is modified for proper use. This can facilitate the safe and effective use of the solution during use, such as during dialysis therapy.

As shown in FIG. 11, the conductive polymer sensor 444 of the present invention can be applied during automated peritoneal dialysis. More specifically, the conductive polymer sensor 444 of the present invention can be attached to the tube member 446 through which a dialysis solution flows to the patient. The dialysis solution is a product of the mixing of solution components that are stored in separate solution bags as previously discussed. The conductive polymer sensor 444 can be attached to a controller 448 or other like device in electrical contact such that the conductivity level and thus the pH level of the solution that is administered to the patient can be monitored as previously discussed. Optionally, at least one additional conductive polymer sensor 450 in an embodiment can also be utilized as shown in FIG. 11. In this regard, the additional sensor(s) can be utilized to monitor the conductivity level of the solution components prior to mixing. This can be utilized to evaluate whether the solution components are maintained at desired pH levels based on a conductivity measurement as discussed above.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A medical device configured to detect dislodgement of an access device during medical treatment of a patient, the medical device comprising:
   a blood circuit connecting the patient to an extracorporeal blood system, wherein the blood circuit includes a blood tubing set having a tube member connected to an access device, and wherein the access device is insertable within the patient such that blood flows between the patient and the extracorporeal blood system via the blood circuit;

an electrode coupled to the blood circuit, and in fluid contact with the blood flowing in the blood circuit, the electrode made of a conductive polymer material including (a) a polymer matrix and a conductive component uniformly dispersed throughout the polymer matrix, wherein the polymer matrix is selected from the group consisting of acrylonitrile butadiene styrene, polycarbonate, acrylic, a cyclo olefin copolymer, a cyclo olefin copolymer blend, a metallocene-based polyethylene and mixtures thereof, or (b) a conductive polymer component selected from the group consisting of polyaniline, polypyrrole, polythiophene, polyethylenedioxthiophene, poly(p-phenylene vinylene) and mixtures thereof; and a controller in electrical communication with the electrode and configured to detect a change in an electrical value responsive to dislodgement of the access device as the blood flows between the patient and the extracorporeal blood system connected to the patient via the access device.

2. The medical device of claim 1, wherein the controller is configured to correct for a deviation from a baseline measurement of the electrical value detected within the conductor loop due to variations in the blood during the medical treatment.

3. The medical device according to claim 1, wherein the controller is capable of measuring a change in impedance in response to dislodgement of the access device.

4. The medical device of claim 1, wherein the conductive component is selected from the group consisting of stainless steel, fillers, carbon black, fibers thereof and mixtures thereof.

5. The medical device of claim 1, further including a coupler incorporated into a portion of the tube member so as to be in fluid contact with the blood flowing through the tube member, wherein the coupler includes a member that extends from at least a portion of an inner surface of the coupler and acts as a stop for a first and second portion of the tube member, thereby allowing a length of a tubing joint that is formed with the coupler and the tube member to be pre-set.

6. The medical device of claim 5, wherein the coupler is injection molded.

7. The medical device of claim 5, wherein the coupler is at least one of solvent bondable, heat sealable, laser weldable, and radio frequency sealable to the tube member.

8. The medical device of claim 5, further including a holding device that includes (i) a base member having a conductive base portion and (ii) an arm member pivotally attached to the base member, the coupler securely positioned between the arm member and the base member of the holding device.

9. The medical device of claim 1, wherein the access device is selected from the group consisting of a needle, a venous needle, and a catheter.

10. A medical device configured to detect dislodgement of an access device during medical treatment, the medical device comprising:

a blood circuit connecting the patient to an extracorporeal blood system, wherein the blood circuit includes a blood tubing set having a first tube member connected to a first access device and a second tube member connected to a second access device, and wherein the first access device and second access device are each insertable within the patient such that blood flows between the patient and the extracorporeal blood system via the blood circuit; and first and second electrodes coupled to the first and second tube members, respectively, and in fluid contact with the blood flowing in the blood circuit, wherein the first and second electrodes are made of a conductive polymer material including (a) a polymer matrix and a conductive component uniformly dispersed throughout the polymer matrix, wherein the polymer matrix is selected from the group consisting of acrylonitrile butadiene styrene, polycarbonate, acrylic, a cyclo olefin copolymer, a cyclo olefin copolymer blend, a metallocene-based polyethylene and mixtures thereof, or (b) a conductive polymer component selected from the group consisting of polyaniline, polypyrrole, polythiophene, polvethylenedioxthiophene, poly(p-phenylene vinylene) and mixtures thereof;

wherein the electrodes define a conductor loop that detects a change in an electrical value responsive to dislodgement of at least one of the access devices as the blood flows between the patient and the extracorporeal blood system connected to the patient via the access devices.

11. The medical device of claim 10, further comprising a controller configured to correct for a deviation from a baseline measurement of the electrical value detected within the conductor loop due to variations in the blood during the medical treatment.

12. The medical device according to claim 11, wherein the controller is capable of measuring a change in impedance in response to dislodgement of at least one of the access devices.

13. The medical device of claim 10, wherein the conductive component is selected from the group consisting of stainless steel, fillers, carbon black, fibers thereof and mixtures thereof.

14. The medical device of claim 10, further including first and second couplers incorporated into a portion of the first and second tube members, respectively, so as to be in fluid contact with the blood flowing through the respective first and second tube members, wherein each coupler includes a member that extends from at least a portion of an inner surface of the coupler and acts as a stop for a first and second portion of the respective tube member, thereby allowing a length of a tubing joint that is formed with the coupler and the respective tube member to be pre-set.

15. The medical device of claim 14, wherein the couplers are injection molded.

16. The medical device of claim 14, wherein the couplers are at least one of solvent bondable, heat sealable, laser weldable, and radio frequency sealable to the tube member.

17. The medical device of claim 14, further including first and second holding devices that each includes (i) a base member having a conductive base portion and (ii) an arm member pivotally attached to the base member, the couplers each securely positioned between the arm member and the base member of the respective holding device.

18. The medical device of claim 10, wherein the first access device and the second access device are selected from the group consisting of a needle, a venous needle, and a catheter.

19. A medical device configured to conduct a medical therapy and to detect an access disconnection during medical therapy, the medical device comprising:

a dialysis machine having one or more connectors including an access device for connecting a patient to the dialysis machine via a blood circuit allowing blood to flow between the patient and the dialysis machine during medical therapy;

an electrode coupled to the blood circuit and in fluid contact with the blood flowing in the blood circuit, the electrode made of a conductive polymer material including (a) a polymer matrix and a conductive component uniformly dispersed throughout the polymer matrix, wherein the polymer matrix is selected from the group consisting of acrylonitrile butadiene styrene, polycarbonate, acrylic, a cyclo olefin copolymer, a cyclo olefin copolymer blend, a metallocene-based polyethylene and mixtures thereof or (b) a conductive polymer component selected from the group consisting of polyaniline, polypyrrole, polythiophene,polyethylendioxthiophene,poly (p-phenylene vinylene) and mixtures,thereof;
and
a controller in electrical communication with the electrode and configured to generate an electrical signal that can be passed into the flowing blood via the electrode during the medical therapy.

20. The medical device of claim 19, wherein the access device is selected from the group consisting of a needle, a venous needle, and a catheter.

21. The medical device of claim 19, wherein the dialysis machine is capable of at least one of hemodialysis, hemodiafiltration, hemofiltration, and continuous renal replacement therapy.

22. The medical device of claim 19, wherein the controller is configured to sound an alarm or shut off a blood pump upon disconnection of the access device.

23. The medical device of claim 19, wherein the conductive component is selected from the group consisting of stainless steel, fillers, carbon black, fibers thereof and mixtures thereof.

24. The medical device of claim 19, further including a coupler incorporated into a portion of the blood circuit so as to be in fluid contact with the blood flowing through the blood circuit, wherein the coupler includes a member that extends from at least a portion of an inner surface of the coupler and acts as a stop for a first and second portion of the blood circuit, thereby allowing a length of a tubing joint that is formed with the coupler and the blood circuit to be pre-set.

25. The medical device of claim 24, wherein the coupler is injection molded.

26. The medical device of claim 24, wherein the coupler is at least one of solvent bondable, heat sealable, laser weldable, and radio frequency sealable to the tube member.

27. The medical device of claim 24, further including (a) a holding device that includes (i) a base member having a conductive base portion and (ii) an arm member pivotally attached to the base member, the coupler securely positioned between the arm member and the base member of the holding device.

28. A medical device configured to detect dislodgement of an access device during medical treatment of a patient, the medical device comprising:
a blood circuit connecting the patient to an extracorporeal blood system, wherein the blood circuit includes a blood tubing set having a tube member connected to an access device, wherein the access device is insertable within the patient such that blood flows between the patient and the extracorporeal blood system via the blood circuit; and
a pair of electrodes coupled to the blood circuit and in fluid contact with the blood flowing in the blood circuit, the electrodes made of a conductive polymer material including (a) a polymer matrix and a conductive component uniformly dispersed throughout the polymer matrix, wherein the polymer matrix is selected from the group consisting of acrylonitrile butadiene styrene, polycarbonate, acrylic, a cyclo olefin copolymer, a cyclo olefin copolymer blend, a metallocene-based polyethylene and mixtures thereof or (b) a conductive polymer component selected from the group consisting of polvaniline, polypyrrole, polythiophene, polvethylenedioxthiophene, polyp-phenylene vinylene) and mixtures thereof;
wherein the electrodes define a conductor loop that detects a change in an electrical value responsive to dislodgement of the access device as the blood flows between the patient and the extracorporeal blood system connected to the patient via the access device.

29. The medical device of claim 28, wherein the conductive component is selected from the group consisting of stainless steel, fillers, carbon black, fibers thereof and mixtures thereof.

* * * * *